United States Patent
Ramjeet et al.

(10) Patent No.: US 11,649,476 B2
(45) Date of Patent: May 16, 2023

(54) FLOW CYTOMETRY DATA PROCESSING FOR ANTIMICROBIAL AGENT SENSIBILITY PREDICTION

(71) Applicant: BIOMÉRIEUX, Marcy l'Etoile (FR)

(72) Inventors: Mahendrasingh Ramjeet, Lyons (FR); Pierre Mahe, Lans en Vercors (FR); Gaël Kaneko, Marcy l'Etoile (FR); Margaux Chapel, Saint Sorlin en Bugey (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 1165 days.

(21) Appl. No.: 16/316,294

(22) PCT Filed: Jul. 6, 2017

(86) PCT No.: PCT/EP2017/066903
§ 371 (c)(1),
(2) Date: Jan. 8, 2019

(87) PCT Pub. No.: WO2018/007504
PCT Pub. Date: Jan. 11, 2018

(65) Prior Publication Data
US 2019/0352693 A1    Nov. 21, 2019

(30) Foreign Application Priority Data
Jul. 8, 2016  (EP) .................... 16178636

(51) Int. Cl.
| | | |
|---|---|---|
| C12Q 1/18 | (2006.01) | |
| G01N 21/64 | (2006.01) | |
| G16B 40/20 | (2019.01) | |
| G16B 40/10 | (2019.01) | |
| G16B 40/00 | (2019.01) | |
| G06N 20/10 | (2019.01) | |

(52) U.S. Cl.
CPC ........... *C12Q 1/18* (2013.01); *G01N 21/6428* (2013.01); *G06N 20/10* (2019.01); *G16B 40/00* (2019.02); *G16B 40/10* (2019.02); *G16B 40/20* (2019.02); *G01N 2021/6439* (2013.01)

(58) Field of Classification Search
CPC .......... C12Q 1/18; G06N 20/10; G16B 40/00; G16B 40/10; G16B 40/20; G01N 21/6428; G01N 2021/6439
USPC ......................................................... 702/19
See application file for complete search history.

(56) References Cited

FOREIGN PATENT DOCUMENTS

| EP | 2821499 A1 | 1/2015 |
| WO | 2012/164547 A1 | 12/2012 |

OTHER PUBLICATIONS

Claude Saint-Ruf, Steve Crussard, Christine Franceschi, Sylvain Orenga, Jasmine Ouattara, Mahendrasingh Ramjeet, JérémySurre, and IvanMatic: Antibiotic Susceptibility Testing of the Gram-Negative Bacteria Based on Flow Cytometry, Frontiers in Microbiology, vol. 7, Jul. 1, 2016 (Year: 2016).*

Tatiane Benaducci, Marcelo Teruyuki Matsumoto, Janaina Cássia Orlandi Sardi, Ana Marisa Fusco-Almeida, Maria José Soares Mendes-Giannini: A flow cytometry method for testing the susceptibility of *Cryptococcus* spp. to amphotericin B, Rev Iberoam Micol. 2015;32(3):159-163 (Year: 2015).*

Huang, T.H., et al., Rapid Cytometric Antibiotic Susceptibility Testing Utilizing Adaptive Multidimensional Statistical Metrics. Analytical Chemistry, vol. 87, No. 3, p. 1941-1949, 2015.

Cuesta, Isabel et al. "Data Mining Validation of Fluconazole Breakpoints Established by the European Committee on Antimicrobial Susceptibility Testing". Antimicrobial Agents and Chemotherapy, vol. 53, No. 7, p. 2949-2954, 2009.

Hutter, Bernd et al. "Prediction of Mechanisms of Action of Antibacterial Compounds by Gene Expression Profiling". Antimicrobial Agents and Chemotherapy, vol. 48, No. 8, p. 2838-2844, 2004.

Goodacre, Royston et al. "Rapid analysis of microbial systems using vibrational spectroscopy and supervised learning methods: application to the discrimination between methicillin-resistant and methicillin-susceptible *Staphylococcus aureus*". SPIE, vol. 3257, p. 220-229, 1998.

(Continued)

*Primary Examiner* — G Steven Vanni
*Assistant Examiner* — Guozhen Liu
(74) *Attorney, Agent, or Firm* — Oliff PLC

(57) ABSTRACT

A method for quantifying the sensibility of a test microorganism to a concentration of an antimicrobial agent includes: preparing two liquid samples including the microorganism, one having the antimicrobial agent and one without; for each sample acquiring, by a flow cytometer, a digital set values including a fluorescence, forward, or side scatter distribution, and computing: a first coordinate value corresponding to the acquired distribution main mode and an acquired distribution first area for values greater than the first coordinate value, and a second coordinate value, greater than the first, for which an acquired distribution second area between the values equals a first area predefined percentage over 50%; computing a ratio according to:

$$Q = \frac{QT(ATB) - \text{Mode}(ATB)}{QT(\text{no } ATB) - \text{Mode}(\text{no } ATB)}$$

where Mode(ATB) and QT(ATB) are the first and second coordinate values with the antimicrobial agent concentration, and Mode(no ATB) and QT(no ATB) are respectively the first and second coordinate values without the antimicrobial agent concentration.

23 Claims, 7 Drawing Sheets

(56) References Cited

OTHER PUBLICATIONS

Saint-Ruf, Claude et al. "Antibiotic Susceptibility Testing of the Gram-Negative Bacteria Based on Flow Cytometry". Frontiers in Microbiology, vol. 7, 2016.

Álvarez-Barrientos, A., et al., "Applications of Flow Cytometry to Clinical Microbiology". Clinical Microbiology Reviews, vol. 13, No. 2, p. 167-195, 2000.

Aghayee, S. "Combination of fluorescence microscopy and nanomotion detection to characterize bacteria". Journal of Molecular Recognition, vol. 26, p. 590-595, 2013.

Shapiro, Howard and Nancy Perlmutter. "Killer Applications: Toward Affordable Rapid Cell-Based Diagnosis for Malaria and Tuberculosis". Cytometry Part B, 74B, p. S152-S164, 2008.

Joux, Fabien and Philippe Lebaron. "Use of fluorescent probes to assess physiological functions of bacteria at single-cell level". Microbes and Infection, vol. 2, p. 1523-1535, 2000.

Martinez, Octavio et al. "The Effect of Some b-Lactam Antibiotics on *Escherichia coli* Studied by Flow Cytometry". Cytometry, vol. 3, No. 2, p. 129-133, 1982.

Pina-Vaz, C., et al. "Safe susceptaibility testing of *Mycobacterium tuberculosis* by flow cytometry with the fluorescent nucleic acid stain SYTO 16". Journal of Medical Microbiology, vol. 54, p. 77-81, 2005.

Cohen, C.Y., and E. Sahar. "Rapid Flow Cytometric Bacterial Detection and Determination of Susceptibility to Amikacin in Body Fluids and Exudates". Journal of Clinical Microbiology, vol. 27, No. 6, p. 1250-1256, 1989.

Kerstens, Monique et al. "Quantification of Candida albicans by flow cytometry using TO-PRO®-3 iodide as a single-stain viability dye". Journal of Microbiological Methods, 2012.

Boi, Paola et al. "Evaluation of *Escherichia coli* Viability by Flow Cytometry: A Method for Determining Bacterial Responses to Antibiotic Exposure". Cytometry Part B, 88B, p. 149-153, 2015.

Nuding, Sabine and Lutz Zabel. "Detection, Identification, and Susceptibility Testing of Bacteria by Flow Cytometry". J Bacteriology Parasitol, S5-005, 2013.

Gauthier, Christian et al. "Rapid antimicrobial susceptibility teting of urinary tract isolates and samples by flow cytometry". Journal of Medical Microbiology, vol. 51, p. 192-200, 2002.

Gant, V.A. et al. "The application of flow cytometry to the study of bacterial responses to antibiotics". Journal of Medical Microbiology, vol. 39, p. 147-154, 1993.

Wickens, H.J. et al. "Flow Cytometric Investigation of Filamentation, Membrane Patency, and Membrane Potential in *Escherichia coli* following Ciprofloxacin Exposure". Antimicrobial Agents and Chemotherapy, vol. 44, No. 3, p. 682-687, 2000.

Renggli, Sabine et al. "The role of auto-fluorescence in flow-cytometric analysis of *Escherichia coli* treated with bactericidal antibiotics". J. Bacteriol, 2013.

Buller, M.T.E. et al. "A flow cytometric study of antibiotic-induced damage and evaluation as a rapid antibiotic susceptibility test for methicillin-resistant *Staphylococcus aureus*". Journal of Antimicrobial Chemotherapy, vol. 40, p. 77-83, 1997.

Jepras, R.I., et al. "Rapid Assessment of Antibiotic Effects on *Escherichia coli* by bis-(1,3-Dibutylbarbituric Acid) Trimethine Oxonol and Flow Cytometry". J. Antimicrobial Agents and Chemotherapy, p. 2001-2005, 1997.

Shrestha, Nabin, et al. "Rapid Differentiation of Methicillin-Resistant and Methicillin-Susceptible *Staphylococcus aureus* by Flow Cytometry after Brief Antibiotic Exposure". Journal of Clinical Microbiology, vol. 49, No. 6, p. 2116-2120, 2011.

Shrestha, N.K., et al. "Immuno-flow cytometry for the rapid identification of *Staphylococcus aureus* and the detection of methicillin resistance". Eur J Clinical Microbiol Infect Dis, vol. 31, No. 8, p. 1879-1882, 2012.

Yuan, Ming and Yi Lin. "Model selection and estimation in regression with grouped variables". Journal of the Royal Statistical Society Series B, vol. 68, Part 1, p. 49-67, 2006.

Bach, F. et al. "Structured Sparsity through Convex Optimization". Statistical Science, vol. 27, No. 4, p. 450-468, 2012.

Aug. 25, 2017 International Search Report issued in International Patent Application No. PCT/EP2017/066903.

Aug. 25, 2017 Written Opinion of the International Searching Authority issued in International Patent Application No. PCT/EP2017/066903.

* cited by examiner

|                         | Number of prediction models |     |     |
|-------------------------|-----|-----|-----|
| Feature vectors         | BPS | GS  | GMS |
| 1D FL1 MFI              | 1   | 1   | 1   |
| 1D FL1 QT               | 4   | 4   | 4   |
| 1D FL1 Binning          | 4   | 4   | 4   |
| 1D SSC Binning          | 4   | 4   | 4   |
| 1D FSC Binning          | 4   | 4   | 4   |
| 2D FSC-SSC Binning      | 4   | 4   | 4   |
| 3D FSC-SSC-FL1 Binning  | 16  | 16  | 16  |
| Total                   | 37  | 37  | 37  |

| Type of prediction models | Best model | Total | mE | Total S | ME | Total R | VME | Score |
|---|---|---|---|---|---|---|---|---|
| 3D FCS-SSC-FL1 Binning (G) | FL1 (40) FSC-SSC (10) | 128 | 11,6 | 71 | 2,3 | 49 | 3 | 28,2 |
| 3D FCS-SSC-FL1 Binning (GMC) | FL1 (10) FSC-SSC (5) | 128 | 13,5 | 71 | 2,2 | 49 | 3,2 | 30,7 |
| 1D SSC Binning (G) | SSC (40) | 128 | 8,4 | 71 | 4,8 | 49 | 3,3 | 31,2 |
| 1D SSC Binning (GMC) | SSC (10) | 128 | 8,1 | 71 | 3 | 49 | 5 | 34,1 |
| 2D FCS-SSC Binning (G) | FSC-SSC (40) | 128 | 10,1 | 71 | 5,9 | 49 | 3,1 | 34,3 |
| 3D FCS-SSC-FL1 Binning (BP) | FL1 (20) FSC-SSC (10) | 128 | 14,6 | 71 | 1,2 | 49 | 4,4 | 34,6 |
| 1D FL1 MFI (GMC) | MFI | 128 | 12,2 | 71 | 5,4 | 49 | 3 | 35 |
| 2D FCS-SSC Binning (GMC) | FSC-SSC (20) | 128 | 11,3 | 71 | 3,7 | 49 | 4,1 | 35,1 |
| 1D FSC Binning (GMC) | FSC (40) | 128 | 13,9 | 71 | 3,8 | 49 | 3,5 | 35,5 |
| 1D FSC Binning (G) | FSC (40) | 128 | 13,5 | 71 | 4,7 | 49 | 3,4 | 36,5 |
| 1D SSC Binning (BP) | SSC (5) | 128 | 17,3 | 71 | 2,3 | 49 | 4 | 37,9 |
| 1D FL1 MFI (G) | MFI | 128 | 15,2 | 71 | 4,3 | 49 | 4,1 | 40,2 |
| 1D FL1 Binning (GMC) | FL1 (40) | 128 | 7,1 | 71 | 6,8 | 49 | 5,4 | 42,3 |
| 2D FCS-SSC Binning (BP) | FSC-SSC (10) | 128 | 15,7 | 71 | 3,1 | 49 | 5,1 | 42,3 |
| 1D FL1 MFI (BP) | MFI | 128 | 18,3 | 71 | 0,6 | 49 | 5,8 | 42,7 |
| 1D FL1 Binning (G) | FL1 (40) | 128 | 10,7 | 71 | 6,1 | 49 | 5,2 | 43,7 |
| 1D FSC Binning (BP) | FSC (10) | 128 | 16,1 | 71 | 3,7 | 49 | 5,2 | 44,3 |
| 1D FL1 Binning (BP) | FL1 (10) | 128 | 12,2 | 71 | 11 | 49 | 4 | 50,2 |
| 1D FL1 QT (G) | (QT 0.99) | 128 | 12,3 | 71 | 13,1 | 49 | 3 | 50,5 |
| 1D FL1 QT (GMC) | (QT 0.99) | 128 | 11,6 | 71 | 14,8 | 49 | 3,1 | 53,6 |
| 1D FL1 QT (BP) | (QT 0.95) | 128 | 16,5 | 71 | 5,3 | 49 | 8,2 | 59,9 |

\* The binning and quantile configurations of the best models are shown in brackets

FIGURE 12

SVM — Reference phenotypes vs Predicted phenotypes:

|  | S | I | R |
|---|---|---|---|
| S | 66 | 2.7 | 2.3 |
| I | 1.3 | 3.7 | 3 |
| R | 3 | 4.6 | 41.4 |

LASSO — Reference phenotypes vs Predicted phenotypes:

|  | S | I | R |
|---|---|---|---|
| S | 65.1 | 1.7 | 4.2 |
| I | 1.1 | 2.9 | 4 |
| R | 3 | 4.1 | 41.9 |

VITEK 2 * — Reference phenotypes vs Predicted phenotypes:

|  | S | I | R |
|---|---|---|---|
| S | 70 | 0 | 1 |
| I | 5 | 3 | 0 |
| R | 6 | 0 | 43 |

| Analytical tool | Best model | Non-relevant [C] | Total | mE | Total S | ME | Total R | VME | Score |
|---|---|---|---|---|---|---|---|---|---|
| SVM | FL1 (40) FSC-SSC (10) | NA | 128 | 11,6 | 71 | 2,3 | 49 | 3 | 28,2 |
| Lasso | FL1 (5) FSC-SSC (20) | 1 and 4 mg/L | 128 | 10,9 | 71 | 4,2 | 49 | 3 | 31,3 |
| VITEK 2 * | NA | NA | 128 | 5 | 71 | 1 | 49 | 6 | 31 |

\* VITEK 2 phenotypes shown were not corrected by the VITEK® 2 Advanced Expert System

FIGURE 13

FLOW CYTOMETRY DATA PROCESSING FOR ANTIMICROBIAL AGENT SENSIBILITY PREDICTION

FIELD OF THE INVENTION

The invention relates to the prediction of sensibility of a microorganism to an antimicrobial agent using flow cytometry, in particular sensibility of a bacteria to an antibiotic.

BACKGROUND OF THE INVENTION

As known per se, two critical concentrations, or "breakpoints", are defined for a antimicrobial agent, and if the minimal inhibitory concentration ("MIC") measured for a microorganism is lower than the first breakpoint the microorganism is susceptible to said agent, if the measured MIC is greater than the second breakpoint the microorganism is resistant to said agent, and if the measured MIC is in between the microorganism is intermediate to said agent. The gold-standard methods currently used in laboratories to evaluate the MIC of a microorganism, and then its sensibility phenotype, to an antimicrobial agent are usually based on measurement of growth inhibition. These techniques include the broth micro-dilution reference method as well as manual and automated alternative methods such as Etest®, disk diffusion, agar dilution, or VITEK 2® instrument, to name a few.

Over the past decades, studies have shown that early bacterial physiological changes can be visualized by a wide array of commercially available fluorescent markers using flow cytometry ("FCM") or microscopic/imaging-based technologies [1-5]. As it is well-known, flow cytometry basically consists in producing a liquid stream carrying aligned particles (e.g. microorganisms) which individually pass through a laser beam, and measuring an optical response to said beam of each of the particles, that is to say its fluorescence, its forward-scattered light and its side-scattered light. In particular FCM-based single-cell analysis can allow fast monitoring of cell counts [6-10] or average fluorescence intensities [11, 12] upon contact with antibiotics. Other antibiotic-induced changes in cell morphology, size, light scattering and auto-fluorescence properties can also be detected by FCM as previously reported in the literature [13-15]. In a recent patent application, the investigation of antibiotic susceptibility profiles through measurement of cell enlargement has been proposed but no robust analysis method is described in order to define discriminating thresholds between phenotypes [16]. So far, only weakly quantitative or arbitrary thresholds mostly based on ratios of distribution averages have been used to differentiate susceptible from resistant populations. In addition, only few effort has been made to combine different signatures such as fluorescence and scattering data in order to address the complexity of the response to antimicrobials. Therefore, a robust strategy that takes full advantage of FCM data information to build robust antibiotic susceptibility prediction algorithms is still lacking, despite numerous attempts to show the value of FCM for fast antibiotic susceptibility testing ("AST").

For example, the patent application WO 2012/164547 A1 [17] describes a method based on the use of breakpoint concentrations. Briefly, after a fast incubation in the presence of antibiotic, bacteria are labeled with a fluorescent marker and analyzed by FCM. The ratios of mean fluorescence intensities ("MFI") between antibiotic-treated and untreated cells, also called staining indexes ("SI"), are calculated for both susceptible and resistance reference breakpoint concentrations. For instance, if a fluorescence marker that labels live cells is used, susceptible strains are expected to exhibit low MFI values when treated with antibiotics. Therefore, the interpretation is as follows: a) if SI<1 at the susceptible reference breakpoint, then a strain is predicted as being susceptible to the antibiotic; b) if SI>1 at the resistance reference breakpoint, then a strain is predicted as being resistant. On the opposite side, if a fluorescent marker that targets cell damage is used, susceptible strains are expected to exhibit high fluorescence values. Consequently, the interpretation is as follows: a) if SI>1 at the susceptible reference breakpoint, then a strain is predicted as being susceptible strain; b) if SI<1 at the resistance reference breakpoint, then a strain is predicted as being resistant.

Other studies have also used a similar approach [11]. The main drawback of this method is that it is based solely on MFI values which are only average distributions that might underestimate or mask signals originating from a small portion of an heterogeneous population. In addition, breakpoint concentrations are defined by reference method based on growth inhibition. However, they don't always correlate with early changes that are detected by FCM. In this regard, other studies have looked at the effect of antibiotics using subinhibitory concentrations [6], concentrations exceeding MIC values [18, 19] or concentrations corresponding to susceptible breakpoints only [12]. Therefore, by focusing only on breakpoint concentrations, important information relative to other concentrations could be lost. Other studies have focused on two-dimensional analysis for better discrimination of populations. Indeed, bi-parametric matrices representing scattering vs. fluorescence [20, 21] or fluorescence 1 vs. fluorescence 2, in case of dual labeling [12], can emphasize subtle differences between populations. Hence, discriminating cutoff values are calculated from the number or percentage of cells that fall in specific regions of the 2D matrix upon contact with antibiotics. However, these regions are often selected qualitatively thereby decreasing the robustness of the method. More recently, an initiative based on 3D analysis of adaptively binned scattering and fluorescence signatures has been published [1]. To date, this is the most advanced study showing an in-depth processing of FCM data to build a prediction algorithm for AST. As listed below, this method has several advantages over previous strategies: a) in comparison to MFI values, the use of binned data can allow specific capture of subtle variations as discussed above; b) the adaptation of the binning strategy to the highest variance dimension allows the selection of the most significant information from the population; c) the 3D-multidimensional analysis combines forward scatter, side scatter and fluorescence data for a more global investigation of antibiotic-induced changes. However, this method might fail to provide a robust analysis for several reasons:

in this study the authors define a discriminating threshold at 99% confidence using a susceptible strain treated with antibiotics at $\frac{1}{16} \times$MIC concentrations. While the bar was set quite low for susceptibility phenotype, their prediction model does not include resistance phenotypes. Indeed, one resistance strain was used only to validate a prediction model that was build using a susceptible strain. Therefore, no discrimination strategy that involves comparison between phenotypes is proposed;

the authors do not describe the detection of intermediate phenotypes;

for a potential application of their prediction model, the authors propose the use of MIC concentrations of their susceptible model strain. This method does not seem to be robust as this antibiotic concentration was not sufficient to clearly detect the susceptibility profile of another strain that exhibited a higher MIC value (ex: Gentamicin). Therefore, this document does not describe any development of a prediction model using a specific concentration and the validation of the method using a different concentration;

the prediction model proposed in this study is based on one single susceptible strain. Due to the heterogeneity of response to antibiotics depending on strains, phenotypes, MIC values, and so on, the robustness of their method cannot be validated.

Despite numerous studies on FCM for fast antibiotic susceptibility testing ("AST"), there is still a need to predict, in a robust manner, the sensibility of microorganisms to a antimicrobial agent.

SUMMARY OF THE INVENTION

In particular, the MFI method fails to robustly quantify subtle effect of a antimicrobial agent. The invention aims at proposing propose a robust quantification of such effect.

To this end, a first object of the invention is a method for quantifying the sensibility of a test microorganism to a concentration of an antimicrobial agent comprising:

preparing at a two liquid samples comprising a population of the test microorganism and a viability fluorescence marker targeting the tested microorganism, one of said liquid sample comprising the antimicrobial agent at said concentration and the another of said liquid samples do not comprising the antimicrobial agent;

for each of said samples of the test microorganism, acquiring, by means of a flow cytometer, a digital set of values comprising a fluorescence distribution or a forward scatter distribution or side scatter distribution of the population of microorganisms in said sample;

for each of said samples, computing of:
  a first coordinate value corresponding to the main mode of the acquired distribution and an first area of the acquired distribution for values greater than the first coordinate value;
  a second coordinate value, greater than said first coordinate value, for which a second area of the acquired distribution between said first and second coordinate values equals a predefined percentage of the first area over 50%,
computing a ratio according to the relation:

$$Q = \frac{QT(ATB) - \text{Mode}(ATB)}{QT(\text{no } ATB) - \text{Mode}(\text{no } ATB)}$$

where Mode(ATB) and QT(ATB) are respectively the first and second coordinate values with said concentration of antimicrobial agent, and Mode(no ATB) and QT(no ATB) are respectively the first and second coordinate values without said concentration of antimicrobial agent.

In other words, the ratio Q is able to catch heterogeneous profiles of the acquired distribution, as one may observe on certain antimicrobial agent that effects only a part of the population of microorganisms contained in a liquid sample. In particular, the more the ratio Q deviate from 1, the more the microorganism is sensible to the antimicrobial agent. According to the MFI method, the tested microorganism would be determined as resistant to the antimicrobial agent, while according to the invention said microorganism would be determined as being sensible.

The invention also aims at proposing a method and a system for predicting the susceptibility, intermediate or resistant phenotype of a microorganism to an antimicrobial agent by flow cytometry, which is fast and robust.

To this end, a second object of the invention is a method for predicting the sensibility phenotype of a test microorganism to an antimicrobial agent amongst susceptible, intermediate and resistant phenotypes, comprising:

A. a learning stage comprising the following steps:
  a. choose a set of microorganisms comprising susceptible, intermediate an resistant phenotype microorganisms, said phenotypes being determined based on a susceptible and a resistant breakpoint concentrations of the antimicrobial agent, and generate a digital set of sensibility phenotypes of said set of microorganisms;
  b. for each microorganism of the set of microorganisms, prepare liquid samples comprising a population of said microorganism, a viability fluorescence marker targeting said microorganism, and the antimicrobial agent, said liquid samples comprising at least two different concentrations of the antimicrobial agent;
  c. for each sample, acquire, by means of a flow cytometer, a digital set of values comprising a fluorescence distribution and/or a forward scatter distribution and/or side scatter distribution of the population of microorganisms in said sample;
  d. for each microorganism of the set of microorganisms, generate, by means of a computer unit, a feature vector based on the sets of values acquired for said microorganism wherein generation of the feature vector comprises, for each of the different concentrations of the antimicrobial agent:
    computing of a first coordinate value corresponding to the main mode of the acquired distribution and an first area of the acquired distribution for values greater than the first coordinate value;
    computing of a second coordinate value, greater than said first coordinate value, for which a second area of the acquired distribution between said first and second coordinate values equals a predefined percentage of the first area over 50%,
    computing a ratio according to the relation:

$$Q = \frac{QT(ATB) - \text{Mode}(ATB)}{QT(\text{no } ATB) - \text{Mode}(\text{no } ATB)}$$

where Mode(ATB) and QT(ATB) are respectively the first and second coordinate values with said concentration of antimicrobial agent, and Mode(no ATB) and QT(no ATB) are respectively the first and second coordinate values without said concentration of antimicrobial agent
  e. learn, by means of a computer unit, a prediction model of the sensibility phenotype to the antimicrobial agent based on the generated feature vectors and the digital set of sensibility phenotypes;
B. a prediction stage comprising the following steps:
  f. prepare liquid samples comprising a population of the test microorganism, the viability fluorescence marker and the antimicrobial agent at the different concentrations;

g. for each sample of the test microorganism, acquire, by means of a flow cytometer, a digital set of values corresponding to the set of values acquired at step c);
h. generate, by means of a computer unit, a feature vector based on the sets of values acquired for the test microorganism, said feature vector corresponding the features vector of step d);
i. predict the sensibility phenotype of the test microorganism, by means of a computer unit storing the prediction model, by applying said model to the feature vector of the test microorganism.

In other words, the prediction model is based on a learning set of data derived from microorganisms having a diversity regarding their phenotypes, and advantageously having a great diversity in terms of Gram/species/genera, concentrations of the antimicrobial agent and response to the antimicrobial agent. A robust prediction model, directly determining the phenotype sensibility amongst susceptible/intermediate/resistant phenotypes may be derived from flow-a cytometry measure of a unknown microorganism, e.g. a bacteria.

According one embodiment:
the prediction model comprises a first prediction model of the susceptible phenotype versus the resistant and intermediate phenotypes, and a second model of the resistant phenotype versus the susceptible and intermediate phenotypes, said first and second prediction models being learned independently; and
the intermediate phenotype is predicted when the first prediction model does not predict the susceptible phenotype and when the second prediction model does not predict the resistant phenotype.

According to another embodiment, the prediction model comprises a first prediction model of the susceptible phenotype versus the resistant and intermediate phenotypes, a second model of the resistant phenotype versus the susceptible and intermediate phenotypes, and third prediction model of the intermediate phenotype versus the susceptible and resistant phenotypes, said first, second and third prediction models being learned independently.

According to one embodiment, the different concentration of the antimicrobial agent define a range comprising the susceptible and resistant breakpoint concentrations.

According one variant, the different concentration of the antimicrobial agent consist respectively in the susceptible and resistant breakpoint concentrations. In another variant, the different concentrations of the antimicrobial agent comprise at least three concentrations, and more particularly at least four concentrations.

According to one embodiment, at least one of the different concentrations of the antimicrobial agent is less than the susceptible breakpoint concentration.

According to one embodiment, the method comprises, at the learning stage, the selection of the different concentrations of the antimicrobial agent by:
selecting a first set of different concentrations comprising the different concentrations of the antimicrobial agent and performing steps b) to f) with all the concentrations of said first set of different concentrations;
learning a prediction model of the sensibility phenotype to the antimicrobial agent based on the generated feature vectors and the digital set of sensibility phenotypes, wherein said learning is performed using a L1-regularised optimization problem trading off precision of the prediction model and complexity of the prediction model, and wherein the different concentrations of the antimicrobial agent are the concentrations of the first set of concentrations that are not discarded by the L1-regularised optimization problem.

In particular, the L1-regularised optimization problem is a L1-regularized logistic regression.

According to one embodiment, the digital set of values comprises a fluorescence distribution over a predefined fluorescence range, and wherein the feature vectors comprises an histogram of the fluorescence distribution over a subdivision of the predefined fluorescence range.

According to one embodiment, the digital set of values comprises a side scatter distribution over a predefined side scatter value range, and wherein the feature vectors comprises an histogram of the side scatter distribution over a subdivision of the predefined side scatter value range.

According to one embodiment, the digital set of values comprises a forward scatter distribution over a predefined forward scatter value range, and wherein the feature vectors comprises an histogram of the forward scatter distribution over a subdivision of the predefined forward scatter value range.

In particular, the predefined percentage is over 70%, preferably equal to 75%, 90%, 95% or 99%.

According to one embodiment, the microorganisms of the set of microorganisms belong to different species and/or genera.

According to one embodiment, the antimicrobial agent is an antibiotic and the microorganisms are bacteria.

Another object of the invention is a method for predicting the sensibility phenotype of a test microorganism to an antimicrobial agent amongst susceptible, intermediate and resistant phenotypes, comprising:
a. prepare liquid samples comprising a population of the test microorganism, the viability fluorescence marker targeting the test microorganism and the antimicrobial agent at different concentrations;
b. for each sample of the test microorganism, acquire, by means of a flow cytometer, a digital set of values comprising a fluorescence distribution and/or a forward scatter distribution and/or side scatter distribution of the population of the test microorganism in said sample;
c. generate, by means of a computer unit, a feature vector based on the sets of values acquired for the test microorganism;
d. predict the sensibility phenotype of the test microorganism, by means of a computing unit storing a prediction model, by applying said model to the feature vector of the test microorganism, wherein the prediction model is learned according the learning phase as described above.

Another object of the invention is a system for predicting the sensibility phenotype of a test microorganism to an antimicrobial agent amongst susceptible, intermediate and resistant phenotypes, comprising:
a flow cytometer for acquiring a digital set of values comprising a fluorescence distribution and/or a forward scatter distribution and/or side scatter distribution of a population of the test microorganism in liquid samples, said samples comprising a viability fluorescence marker targeting the test microorganism and different concentrations of the antimicrobial agent and;
a computer unit configured for
storing a prediction model learned according the learning phase as described above;
generating a feature vector based on the sets of values acquired for the test microorganism; and predicting the sensibility phenotype of the test microorganism by applying the prediction model to the feature vector of the test microorganism.

Another object of the invention is a computer readable medium storing instruction for executing a method performed by a computer, the method comprising the prediction of the sensibility phenotype of a test microorganism to an antimicrobial agent amongst susceptible, intermediate and resistant phenotypes, said prediction comprising:

generating a feature vector based on sets of values acquired for a test microorganism, said sets comprising a fluorescence distribution and/or a forward scatter distribution and/or side scatter distribution of a population of the test microorganism in liquid samples acquired by a flow cytometer; and predicting the sensibility phenotype of the test microorganism by applying a prediction model to the feature vector of the test microorganism, wherein the prediction model learned according the learning phase as described above.

BRIEF DESCRIPTION OF THE DRAWINGS

The invention will be better understood from the following non-limiting description, in connection with the accompanying drawings, among which:

FIG. 12 is a table of the classification of prediction models for Ceftazidime; and FIG. 13 is a schematic comparison of performance of 3D prediction models (GS) and VITEK 2.

DETAILED DESCRIPTION

Unless explicitly stated otherwise, greater means greater or equal and less means less or equal.

Figure 1:
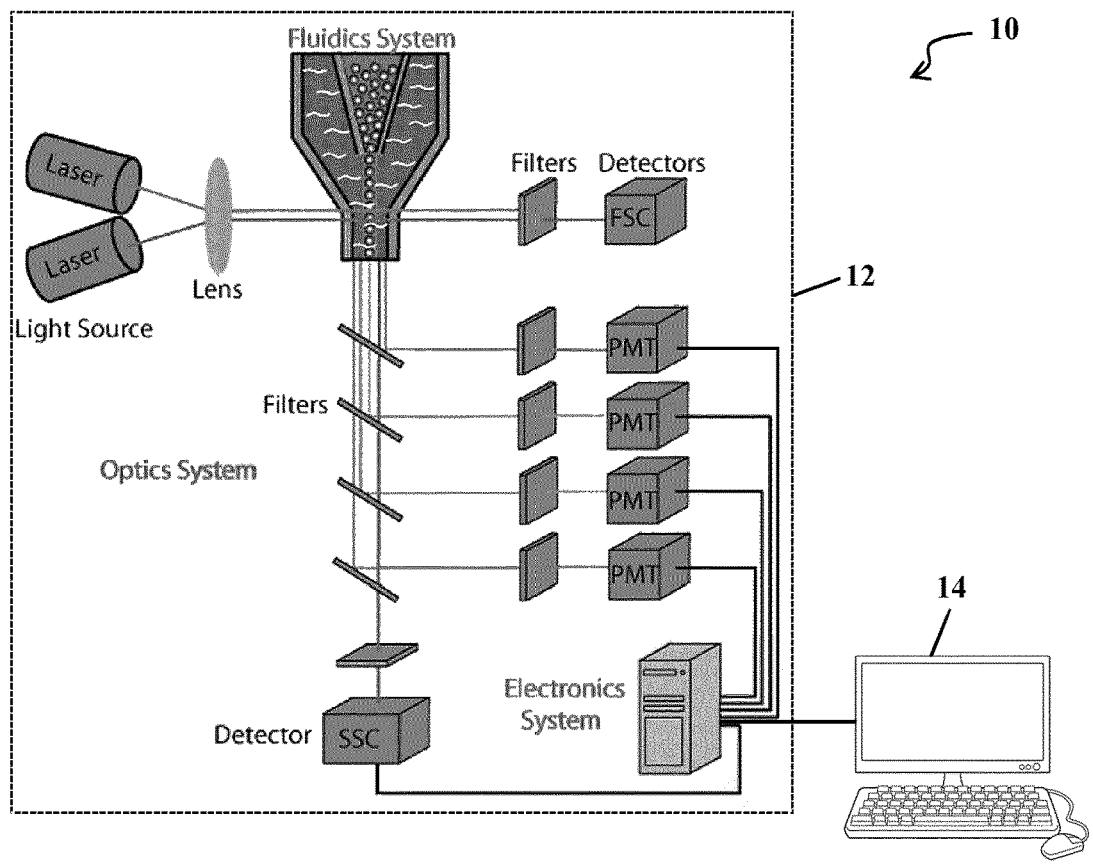
FIG. 1 is a schematic view of a flow-cytometry system according to the invention.

Referring to FIG. 1, a flow-cytometry system 10 comprises a flow-cytometer 12 and a computer unit 14 for processing data output by the flow-cytometer 12 to learn prediction model and/or predict sensibility phenotypes of microorganisms to antimicrobial agents. The flow-cytometer 12 comprises a fluidic system, at least one light source, an optical system comprising excitation optics and collection optics, and an electronic system. The fluidic system is designed to transport the microorganisms of the liquid sample one at a time to an interrogation point where a beam of the light source intersects. At this point light is scattered and refracted by the microorganisms and light scatter is collected by the optic system at two angles where they are acquired by detectors, that is to say the "Forward scatter" (FSC), which is a measurement of diffracted light in the direction of the light source, and the "Side scatter" (SSC), which is collected around 90° from the light beam. Moreover, the light source(s) is/are designed to excite fluorochromes so that fluorescence of microorganisms is also acquired through the optical system by detectors. For the population of microorganisms contains in the liquid sample, a FSC distribution, a SSC distribution and a fluorescence distribution are the acquired and stored in an electronics systems which also drives the flow cytometer operation. Flow-cytometry being well-known, it won't be further detailed. For example, the flow-cytometer is a "Cyflow® Space flow cytometer" from Partec GmbH. The FSC, SSC and fluorescence distributions are communicated to the computer unit 14, for example a personal computer, a tablet, a smartphone, a server, and more generally any system comprising one or more microprocessors and/or one or more microcontrollers, e.g. a digital signal processor, and/or one more programmable logic device, configured to implement a digital processing of the distributions generated by the flow-cytometers 12. The computer unit 14 comprises computer memories (RAM, ROM, cache memory, mass memory) for the storing the acquired distributions, instructions for executing the method according to the invention, and intermediate and final computation, in particular the antibiotic sensibility of the microorganisms. The computer units further comprises a screen for displaying said sensibility to users. While the computer unit has been described as a distinct entity from the electronic system of the flow-cytometer, the computer unit and the electronic systems may be implemented by a unique unit.

Figure 2A:
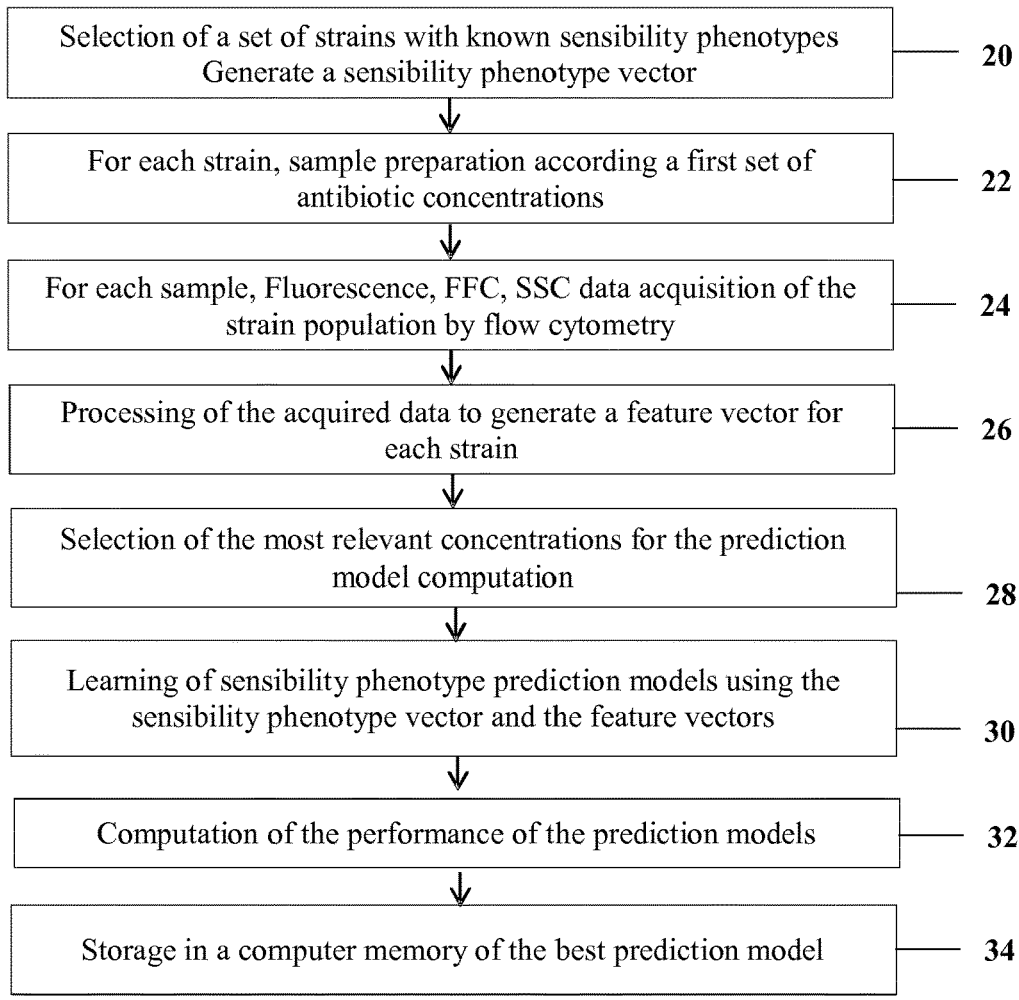
FIG. 2A is a flowchart of a learning stage according to the invention.
Figure 2B:
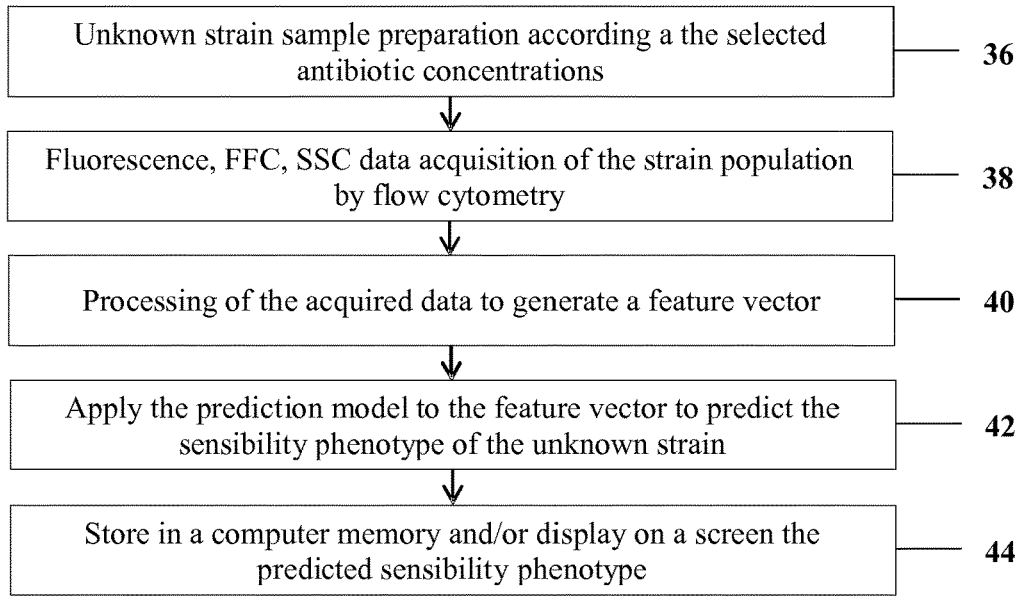
FIG. 2B is a flowchart of a prediction stage according to the invention.

A method to predict the sensibility to an antibiotic of a bacterial strain is now described in relation to FIG. 2, the method comprising a learning stage (FIG. 2A) and a prediction stage (FIG. 2B).

The learning stage aims a determining antibiotic sensibility phenotype patterns in the FSC, SSC and fluorescence distributions of a set of different known strains, in particular susceptible phenotype (S) strains, intermediate phenotype (I) strains and resistant phenotype (R) strains, the sensibility phenotype to the antibiotic of each strain being known and determined according the EUCAT or CLSI nomenclature for example. Advantageously, the patterns are determined to be independent as far of possible of the strains. To this end, the set of strains comprises more than 100 hundred strains from different species and/or genera.

The learning stage thus begins, in 20, by the selection of said set of strains $\{S_1, \ldots, S_n\}$, where n is the number of strains, and by storing their sensibility phenotypes in the computer unit 14, the phenotypes, e.g. in the form of a digital phenotype vector $(P_1 \ldots P_N)$, where $\forall i \in [1, n]$, $P_i$ is the sensibility phenotype of strain $S_i$ to the antibiotic, i.e. $P_i$=R (resistant), I (intermediate) or S (susceptible). The antibiotic breakpoints $BP_S$ (susceptible breakpoint) and $BP_R$ (resistant breakpoint) of the antibiotic.

In a next step 22, liquid samples with different concentrations $\{C_1, \ldots, C_m\}$ of the antibiotic are prepared for each of the selected strains $S_i$, where $C_1$=0 (no antibiotic) and m>2 is the number of non-null concentrations of antibiotic.

Figure 3:
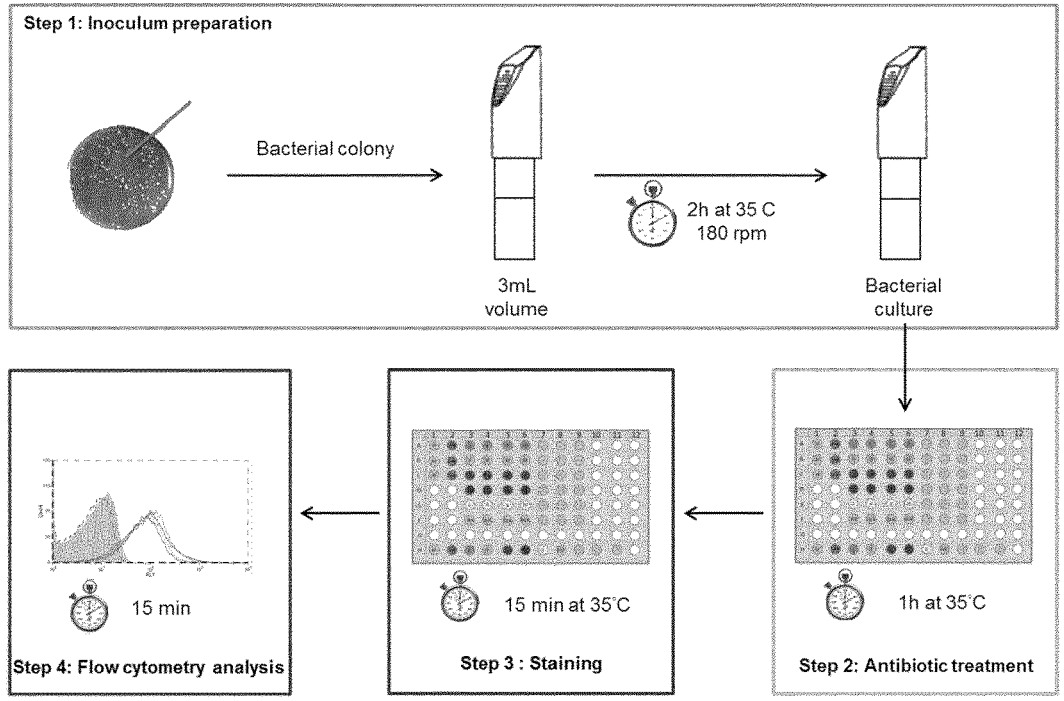
FIG. 3 is a flowchart of a FCM-AST protocol according to the invention detailing the sample preparation.

Said concentrations are stored in the computer unit 14. In particular, as illustrated in FIG. 3, bacterial colonies of the strain are grown and used to make an inoculum. After 2 h growth at 35° C. with shaking at 180 rpm, the resulting exponential phase bacterial culture is normalized at 0.5 McF and used to inoculate wells of a microtiterplate supplemented with antibiotics at the different concentrations $\{C_1, \ldots, C_m\}$. After 1 h of incubation at 35° C., a membrane depolarization fluorescent marker, for example (Bis-(1,3-Dibutylbarbituric Acid)Trimethine Oxonol), also known as "DiBAC4(3)", is added to the wells at a final concentration of 0.5 µg/ml. An additional 15 min incubation with the marker is at 35° C. is then carried out. The concentrations $\{C_1, \ldots, C_m\}$ are chosen such that the range $[BP_S, BP_R]$ is included or equal to the range $[C_2, C_m]$ of non-null concentrations.

In the step 24, a FCM acquisition is performed for each sample by means of the flow-cytometer 12 and the corresponding FSC, SSC and fluorescence distributions stored in the computer unit 14. For each strain $S_i$, and for each concentration $C_1$, a FSC distribution "$FSC_{i,j}$", a SSC distribution "$SSC_{i,j}$" and a fluorescence distribution "$FI_{i,j}$" are thus stored in the computer unit 14, e.g. in the form of digital vectors.

Figures 4, 5:
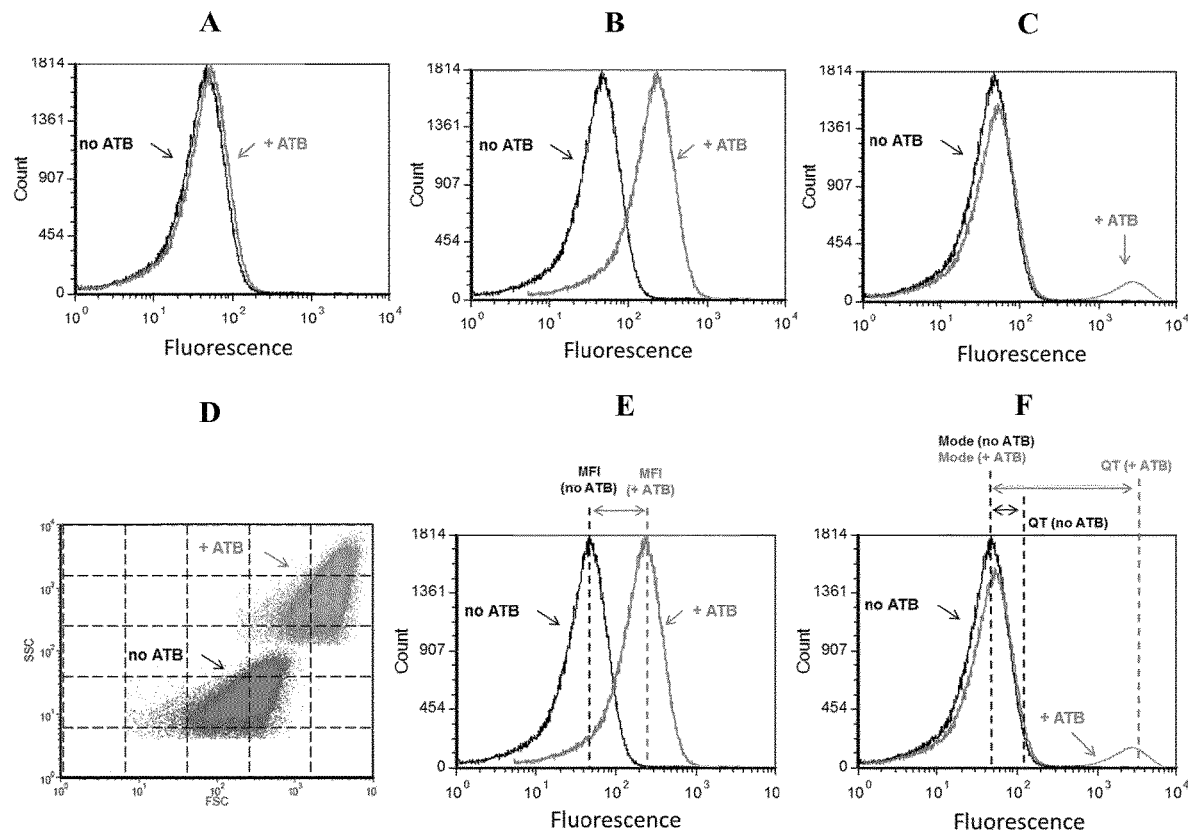
FIG. 4 is a schematic representation of population distribution profiles and the methods used to generate feature vectors.
FIG. 5 is a schematic representation of the phenotype discrimination strategies used to build phenotype prediction models.

A processing of said distribution is performed, in 26, by the computer unit 14 in order to generate at least one feature vector $X_{i,j}$ for each set of distributions $\{FSC_{i,j}, SSC_{i,j}, FI_{i,j}\}$. The generated features vectors $X_{i,j}$ quantify the changes that occur within the bacterial populations following incubation with antibiotic, and are combined with digital phenotype vector $(P_1 \ldots P_N)$ to find phenotype patterns as described latter. In particular, feature vectors based on three methods, that is to say, a mean fluorescence intensity (MFI) method, a binning method and a quantile (QT) method. FIG. 4 is schematic representation of population distribution profiles and the methods used to generate feature vectors. In FIG. 4, "ATB" refers to a sample with a non-null concentration of antibiotic ($C_{j>1}$) and "no ATB" refers to a sample with no antibiotic ($C_1$).

In the mean fluorescence intensity method, as illustrated in FIG. 4E, a feature vector $X_{i,j}$ is computed for a each non-null concentration $C_{j>1}$ according to the relation:

$$X_{i,j>1} = MFI(i, j>1) = \frac{\overline{FI_{i,j>1}}}{\overline{FI_{i,1}}}$$

where $\overline{FI_{i,j>1}}$ and $\overline{FI_{i,1}}$ are respectively the mean values of distributions $FI_{i,j>1}$ and $FI_{i,1}$.

In figures FIGS. 4A, 4B and 4C, monoparametric histogram show three main fluorescence distributions observed for antibiotic-treated and untreated bacterial populations. When compared to the distribution of untreated populations, antibiotic-treated bacteria exhibit either no or slight fluorescence shift (A), a fluorescence shift of the entire population (B) or a fluorescence shift of only one small portion of the population (C). The more the feature vector $X_{i,j>1}$ differs from 1, the more the strain is susceptible to the antibiotic. Similar distribution profiles can also be observed for SSC and FSC (not shown).

The binning method is performed on biparametric FSC-SSC distributions and on monoparametric ("1D") distributions of fluorescence, FSC and SSC. In particular, the range of a distribution (e.g. fluorescence) is divided in intervals, or "bins", and the intensities of the distribution in each bin are summed, or "binned". For example, referring to FIG. 4D, a biparametric ("2D") dot plot is shows the difference in scattering profiles between treated and untreated bacterial populations. In this figure, a grid of 5×5 (25 bins) is applied to the 2D plot. The number of events in each bin is recorded to generate a set of values defined as feature vector. Binning is performed on biparametric FSC-SSC distributions as shown in this example and on monoparametric distributions of fluorescence, FSC and SSC. More precisely, these vectors were obtained as follows:

- binning of 1D SSC or FSC distribution: the dynamic range of the signal (e.g. [1, 10000]), is cut in 5, 10, 20 or 40 bins of the size on a logarithmic scale. The proportion of events falling in each bin was then used to represent the entire distribution;
- binning of 2D SSC/FSC distributions: the same procedure is applied on the bi-dimensional space defined by the two scattering signals, which is therefore discretized into 5×5=25, 10×10=100, 20×20=400 or 40×40=1600 bins;
- binning of 1D fluorescence signal: the same procedure as the one for the 1D scattering signals is applied, with the notable exception that only the part of the distribution that is above its mode (i.e: above the main pic at non null intensity) is considered. The remaining part of the distribution is not considered because the fluorescence distribution exhibits a peak at null intensity that could greatly vary in its amplitude, which could therefore be detrimental to the binning representation.

In quantile method, as illustrated in FIG. 4F, a ratio of fluorescence values at each quantile of a set of quantiles is calculated as follows:

$$X_{i,j>1} = Q(i, j>1, q) = \frac{QT(FI_{i,j>1}, q) - \mathrm{Mode}(FI_{i,j>1})}{QT(FI_{i,1}, q) - \mathrm{Mode}(FI_{i,1})}$$

where $\mathrm{Mode}(FI_{i,j>1})$ is the fluorescence value of the main non-null pic of the fluorescence distribution $FI_{i,j>1}$, i.e. the fluorescence intensity corresponding to the maximum number of events, $QT(FI_{i,j>1},q)$ is the fluorescence value such that the area of the fluorescence distribution between said two values equal q % of the total area of the fluorescence distribution for fluorescence values above the mode, and Mode(no ATB) and QT (no ATB) are respectively analogue values for fluorescence distribution with null concentration $C_1$. Quantiles q are above 70%, in particular equal to 75%, 90%, 95% and 99% of the area under the curve from left to right.

The quantile method is designed to allow more efficient detection of subtle changes in the fluorescence distribution of populations upon contact with antibiotics. Indeed, for a given strain treated with an antibiotic, three main distribution profiles that can be observed are represented in FIG. 4. In heterogeneous fluorescence distributions where only a small part of the population exhibit a strong fluorescence (FIGS. 4C and 4F), the MFI method might not be appropriate since the signal will be dominated by the non-fluorescent population. In this case the quantile method could allow to capture the signal originating from the small population.

Therefore, for a given strain treated with one concentration of antibiotic, the following feature vectors are generated by the computer unit 14:

4 sets of values obtained from 1D fluorescence distributions (binned data);

4 sets of values obtained from 1D SSC distributions (binned data);

4 sets of values obtained from 1D FSC distributions (binned data);

4 sets of values corresponding to 2D FSC-SSC distributions (binned data)

1 ratio of MFI;

4 ratios of quantiles Q; and 16 sets of values obtained from the combinations of 2D FSC-SSC distributions and 1D fluorescence distributions (3D models, binned data).

In the next step 28 of the learning stage, the computer units selects amongst the concentration set $\{C_1, \ldots, C_m\}$, the concentrations which are the most relevant for the phenotype prediction. To this end, the unit 14 learns at least one adaptive prediction model of the sensibility phenotypes based on the generated feature vectors $X_{i,j}$ and the vector of phenotypes $(P_1 \ldots P_N)$, in particular using supervised learning based on a L1-regularised optimization problem, as it is described later. In particular, the L1-regularized problem trades-off between the precision of the prediction model and the complexity of the model. Reducing the number of concentrations shorten the sample preparation, the flow-cytometry acquisition and data processing during the phenotype prediction of an unknown strain.

Based on the selected concentrations or the whole set $\{C_1, \ldots, C_m\}$, the computer unit 14 learns, in a step 30, prediction model of the sensibility phenotypes based on the generated feature vectors $X_{i,j}$ and the vector of phenotypes $(P_1 \ldots P_N)$, in particular using supervised learning, e.g. a support vector machine (SVM) learning. In particular, all the 1D, 2D and 3D feature vectors generated are processed using the three different phenotype discrimination strategies detailed in FIG. 5:

The breakpoint-based strategy (BPS). The BPS strategy is based on two matrices that predict S and R phenotypes, respectively. Intermediate phenotypes are predicted by elimination when they don't fall in any of the two matrices;

The global strategy (GS). The GS strategy is also based on two matrices for S and R and Intermediate phenotypes are also predicted by elimination. As opposed to the BPS strategy, GS can build prediction models by processing data from more than one antibiotic concentration in each matrix.

The global multiclass strategy (GMS). The GMC strategy is based on 3 matrices that predict S, I and R phenotypes, respectively. Similar to GS, the GMC strategy can also process data from more than one antibiotic concentration in each matrix.

As described in FIG. 5, in which 4 concentrations C1, C2, C3 and C4 are exemplified: (A) in the breakpoint-based strategy (BPS), feature vectors generated following FCM analysis of strains are processed in two matrices. The first matrix processes the feature vectors generated after incubation of strains with a concentration of antibiotic corresponding to the susceptible reference breakpoint (feature vector for $BP_S$). In this matrix, a cutoff is calculated to discriminate S phenotype from I or R phenotypes. The second matrix processes the feature vectors generated following incubation of strains with a concentration of antibiotic corresponding to the resistance reference breakpoint (feature vector for $BP_R$). In this matrix, another cutoff is calculated to discriminate R phenotype from S or I phenotypes. Strains that are not predicted as S in the first matrix and R in the second matrix are classified as I. (B) The global strategy (GS) is also based on two matrices that predict S and R phenotypes, respectively. Both matrices process feature vectors generated following incubation of strains with all concentrations of antibiotics investigated (ex: C1 to C4). (C) The global multiclass strategy (GMS) is based on three matrices. Each phenotype is differentiated in a separate matrix from the two other phenotypes. This strategy also process feature vectors generated for all antibiotic concentrations investigated.

MIC concentrations determined by the reference microdilution method is not always correlated with the concentrations that induce the most significant early changes by FCM using a specific protocol. In this regard, other FCM-based studies have rather investigated the effect of antibiotics using subinhibitory concentrations [6] or concentrations exceeding MIC values [18, 19]. Therefore, by using only the BPS strategy with the susceptible and the resistant breakpoint concentrations, important information that originate from neighboring antibiotic concentrations may be missed. In the global strategies according to the invention (GS and GMS), the prediction models are built on additional concentrations in order to integrate additional antibiotic-induced changes, if any, that may help to better discriminate between phenotypes.

To build the predictive models, two different strategies were set-up depending on the nature of the data representation:

for the BPS strategy operating on the fluorescence signal represented by a MFI or the quantile-based indicator Q, each microorganism was represented by a single value, this values being not the same to build the models in charge of predicting S and R phenotypes because they were computed from different antibiotic concentrations. The classification rule has a simple form in this case and simply amounted to setting a threshold on the MFI or Q. To optimize this threshold, a ROC curve analysis is used, as detailed below;

in all other cases, each microorganism was represented by several values (e.g., several MFI or Q values for the GS and GMC strategies, or a vector containing one or several binned distribution(s) for the BPS, GS and GMC strategies). In these cases, the Support Vector Machine (SVM) algorithm is implemented by the computer unit to learn a classification rule converting such multi-dimensional feature vectors into a classification rule, as detailed below.

The procedure to build the BPS, GS and GMC models is the same in both cases:

for the BPS and GS strategy, two models in charge of identifying S and R strains are independently built. Both models are binary classification models, the first one seeking to separate S strains from {I and R} strains and the second one seeking to separate R strains from {S and I}. The difference between the BPS and GS strategy solely resided in the amount of information provided to the learning algorithm. With the BPS strategy, the sole antibiotic concentration considered to learn each of the {R vs S-I} and {S vs R-I} model was the one that corresponded to the associated breakpoint. This therefore meant that the data provided to the algorithm to learn each model was not the same. Conversely, in the GS strategy, every antibiotic concentration available is considered to learn each model. This therefore mean that the data provided to the algorithm to learn each model is the same, and is typically m-1 times longer than the one provided to the BPS strategy, advantageously m-1=4, 4 concentrations being considered to characterize strains to a given antibiotic);

For the GMC strategy, a "one versus all" SVM multiclass model is built to directly identify R, S and I strains. For that purpose, three models are constructed, each in charge of separating strains of one category from strains of the two other ones. This contrasted with the above approaches in which I strains are identified by elimination (strains that were neither classified as R nor S).

To build more efficient classification rules, the parameters involved in the learning algorithms are optimized, e.g. the regularization parameter (sometimes called "C") of the SVM for multi-dimensional signal representations, the threshold to consider on the MFI or Q values (mono-dimensional representation) in a receiver operating characteristic (ROC) curve. In particular, those parameters are optimized by cross-validation, the general principle thereof being sketched as follows:
Split the dataset in a pre-determined number K of even subsets, or "folds", with K typically set to 5 or 10;
Carry out an iterative procedure in which:
    Leave aside one of the K subsets of the data
    Learn the classification model from the (K−1) remaining subsets, for different values of the model parameter to optimize
    Evaluate the predictions on the held out subset, for the different candidate models, corresponding to the different values of the model parameter.
Evaluate the classification performance measured on the entire dataset for the different candidate values of the model parameter;
Choose the value maximizing the classification performance.

The final model are then built from the entire dataset using the optimal parameter values, and are used to make predictions on new samples.

To learn the regularization parameter of the SVM involved in the multi-dimensional representations of the BPS, GS and GMC strategies, we proceeded this way using the grid of candidate value defined as $\{10^{-4}, 10^{-3.5}, 10^{-3}, \ldots, 10^{3}, 10^{3.5}, 10^{4}\}$. In the case of the uni-dimensional representation of the MFI- and R-based BPS strategy, the following process is implemented:
To define candidate thresholds, a ROC curve is first built for each of the two models in charge of identifying R and S strains from the remaining ones;
then 6 candidate thresholds corresponding to true positive rates (or sensitivities) of $\{0.7, 0.75, 0.8, 0.85, 0.9, 0.95\}$ are extracted, the positive class corresponding to the class targeted by each model (i.e., R for the model in charge of identifying R strains and S for the other one).

In a next step 32, the performance of each of the prediction models is thereafter computed by the unit 14. In particular, the prediction models generated are evaluated through cross validation and the number of phenotype prediction errors recorded are classified as follows:
minor errors (mE)=I predicted S or R, S predicted I or R predicted I;
major errors (ME)=S predicted R;
very major errors (VME)=R predicted S To evaluate the classification performance of the various models considered, a nested cross-validation scheme is implemented in which the dataset is split into K subsets and an iterative procedure is carried out in which:
the parameters involved in the model using (K−1) subsets of the dataset are optimized. For this purpose, we rely on the cross-validation procedure described previously;
the predictions on the remaining subset is evaluated.

This procedure is standard to evaluate performance on classification models, and has the interest on integrating the step of parameter optimization in the estimation of the model performance. In practice, this procedure is repeated several times, e.g. 10 times, in order to be robust to the random splitting of the dataset into subsets, and in order to consider the average performance obtained across repetitions. A score based on the number of prediction errors is computed by the computer unit 14 for each prediction model using the following formula:

Score=Number($mE$)×$p1$+Number($ME$)×$p2$+Number($VME$)×$p3$ where $p1>p2>p3$ are positive number, for example respectively equal to 1, 2 and 4.

Prediction errors are thus rated according to their relative clinical importance, e.g. as defined in US Federal Drug Administration acceptance criteria. The model exhibiting the lowest score is defined as the best prediction model. The best prediction model is then stored, in a step 34, in a computer memory.

Turning back to concentration selection step 28, the global strategies (GS and GMS) aim to integrate additional information to improve discrimination potential of prediction models. However, depending on the bug/drug combination investigated, additional concentrations can either improve, reduce or have no effect on the discrimination potential of prediction models. For instance, high concentrations of antibiotics can induce rapid lysis of susceptible cells leading to a loss of information in FCM analysis. Concentrations higher than resistant breakpoint concentrations can also damage cells exhibiting low level of resistance and change their FCM resistance profiles into susceptible ones. In the case where our global strategies provide better prediction models than the BPS, the question remains as to what are the most relevant concentrations to be used. For instance, if 4 concentrations are investigated (C1, C2, C3 and C4), 15 theoretical combinations of relevant concentrations are possible for a given antibiotic. In order to assess which one of this combination is the most relevant, a L1-regularized Logistic-Regression, or Lasso Logistic-Regression, is implemented to build prediction models that only consider the most relevant concentrations. The main advantage of this method is that it can allow:
to reduce the amount of reagent (ex: if only 1 out 4 concentrations tested is relevant for optimal discrimination);
to reduce the time of FCM acquisition (ex: Less tubes or wells will have to be analyzed if just one concentration is relevant);
to select the most appropriate concentrations (ex: if the most relevant concentrations are not necessarily breakpoint concentrations)

Hence, this tool can help to optimize the development of a FCM protocol for a given bug/drug combination and a given viability marker. As it is well-known, the L1-regularized Logistic Regression is very similar to the SVM. The main difference resides in a different regularization function. The standard SVM includes a regularization term defined in terms of the Euclidean or L2 norm of its weight vector (e.g.: $\|w\|^2 = (\Sigma(w_i)^2)^{1/2}$, where w is the vector of the decision variable in a SVM learning). Considering the L1 norm instead of the Euclidean norm amounts to considering the quantity $\|w\|_1 = \Sigma|w_i|$ as regularization term. Both definitions have the effect of limiting the magnitude of the weights, which is crucial to learn in high dimensions, but the L1 penalty has a well-known "sparsity" effect leading to weights that can be not only small, but exactly equal to zero, which will never happen with the L2 penalty. As a result, using this penalty in a SVM (or a Logistic Regression) allows to automatically select variables that are relevant for the model. In this context, this allows to automatically discard concentrations that may not be informative. Applying the L1 penalty to multivariate MFI and R representations is straightforward. To apply the L1 penalty to binning data gathering several antibiotic concentrations, a more advanced analytical tool called the "group lasso" penalty is performed. Indeed, a concentration may be discarded if all the features corresponding to its binning representation are jointly set to zero. In order to achieve this, a grouping structure, regrouping all the features coming from a given concentration in the same group, is used. The group-lasso penalty then achieves sparsity at the group level, hence at the concentration level. This algorithm is for example described in [22,23].

It is now described in reference to FIG. 2B, a prediction stage according to the invention. This prediction stage aims at determining the sensibility phenotype of a particular strain, e.g. an unknown strain or a strain whose species is known but whose sensibility phenotype is unknown. The prediction stage is embodied using a system analogue to the system described in the FIG. 1, e.g. installed in a clinical laboratory, that is to say a system comprising a flow cytometer and a computer unit connected to the flow cytometer storing in a memory the prediction model selected during the learning stage. The flow cytometer is advantageously of the same model and is operated with the same control parameters than the flow cytometer used in the learning state. The computer unit may be for example computer located at the same place than the flow cytometer or a server located at a remote location which performs a cloud computing based on the data communicated by the flow cytometer over a communication network, e.g. the Internet.

The prediction stage begins, in a step 36, by the preparation of liquid samples of the strains as described above with the concentrations corresponding to the prediction model stored in the computer unit, e.g. the whole set of concentrations or the selected concentrations. In the following step 38, the FFC, SSC and fluorescence distributions are acquired and stored in the computing unit. The latter then generates, in 40, feature vectors having the same format than the ones used to learn the prediction model, and the, in 42, the computer unit applies the prediction model to the generated feature vectors, thereby outputting a sensibility phenotype S, I or R for the tested strain. The result of the prediction is then store in a computer memory and/or display on a screen in a step 44.

While it has been described a systematic approach to learn the best model amongst a wide variety of predictions models, the learning stage may perform the learning of a single prediction model, for example in the case where one knows beforehand which type of model is the best for a particular antibiotic. For example, quantile ratio have very good performance for antibiotic inducing heterogonous fluorescence profiles as illustrated in FIG. 4C. In such case, only the distribution necessary for the feature vectors generation may be acquired, only the feature vectors used for the prediction model learning and implementation are generated (e.g. at least one of the quantile ratios or all the quantile ratios), and only the selected prediction model is learned and implemented.

Moreover, the quantile ratio Q may be used alone to quantify the effect of the antibiotic on a bacterial. In particular, a method for quantifying this effect comprises the preparation of a first sample with a concentration of the antibiotic, of a second sample with non antiobiotic, and the computation by the computing unit of the ratio Q for this two sample has described above. The ratio Q may be for example stored and/or displayed on a screen to the attention of a user.

Moreover, the quantile method may also be implemented on FSC or SSC distributions. In such case, optionally and advantageously, no fluorescent marker is used.

The invention also applies to the following:
FCM-AST from biological samples or microbial extracts;
Other viability markers or multi-labelling can be used;
Can be applied to all species and antibiotics/antifungals;
The rating of errors can be adjusted to enhance the prediction of a particular phenotype;
The quantile method can also be applied to FSC and SSC monoparametric distributions;
The quantile method can also be used to detect heterogeneous populations (ex: hVISA);
More than 4 configurations can be investigated for Binning and Quantile methods;
3D models can also be built by combining 1D feature vectors obtained from the binning method;
3D models can also be built by combining 1D feature vectors obtained from quantile or MFI methods;
2D models including scattering and fluorescence can also be investigated;
Autofluorescence of cells can also be added as an additional parameter for analysis.

While it has been described the sensibility phenotype prediction of a bacteria to an antibiotic, the present invention also applies to yeast and fungus.

Performance Evaluation of Phenotype Prediction Algorithms

Figure 6:
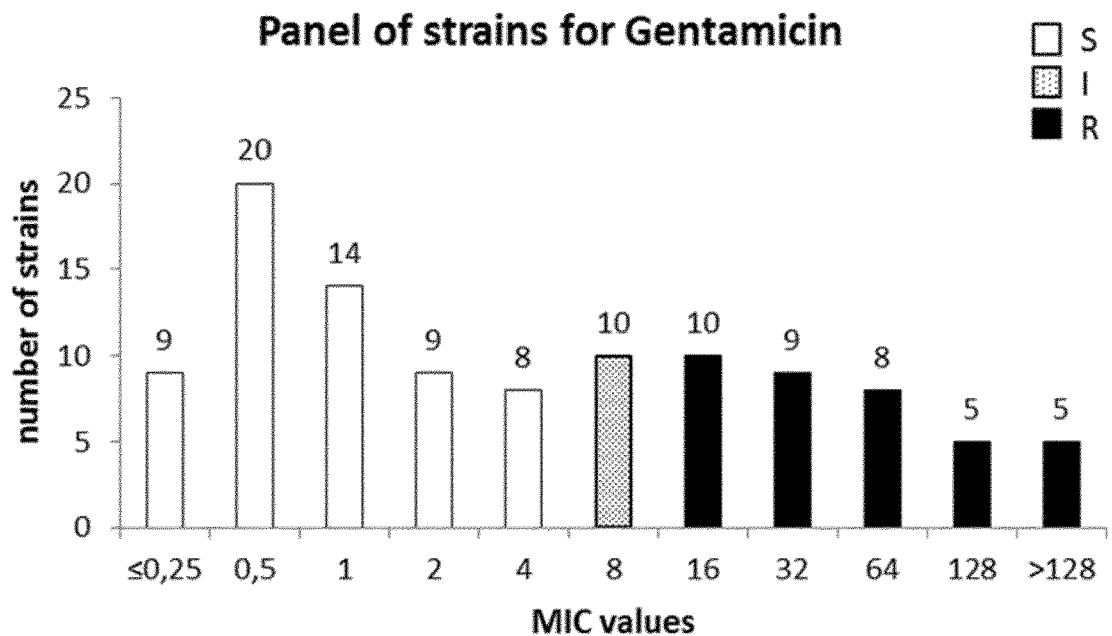
FIG. 6 is a schematic representation of the panel of strains according to their MICs for Gentamicin.

A. Experiment 1: Evaluation of Quantile-Based Prediction Models for Heterogeneous Fluorescence Distributions A.i. Fluorescence Distribution Profiles of Gentamicin-Treated Strains The experiment was performed as described in the following lines:
A panel of 107 Enterobacteriaceae strains (FIG. 6: Distribution of the panel of strains according to their MICs for Gentamicin) were treated with 0, 2, 4 and 8 mg/L of Gentamicin following the protocol described in FIG. 3 and analyzed by FCM. Reference phenotypes of all strains were determined by broth microdilution method according to CLSI breakpoints;
Fluorescence distribution were observed for all strains and classified based on their profiles;
Prediction models were generated from FCM data and the performance was evaluated as described above.

Figure 7:
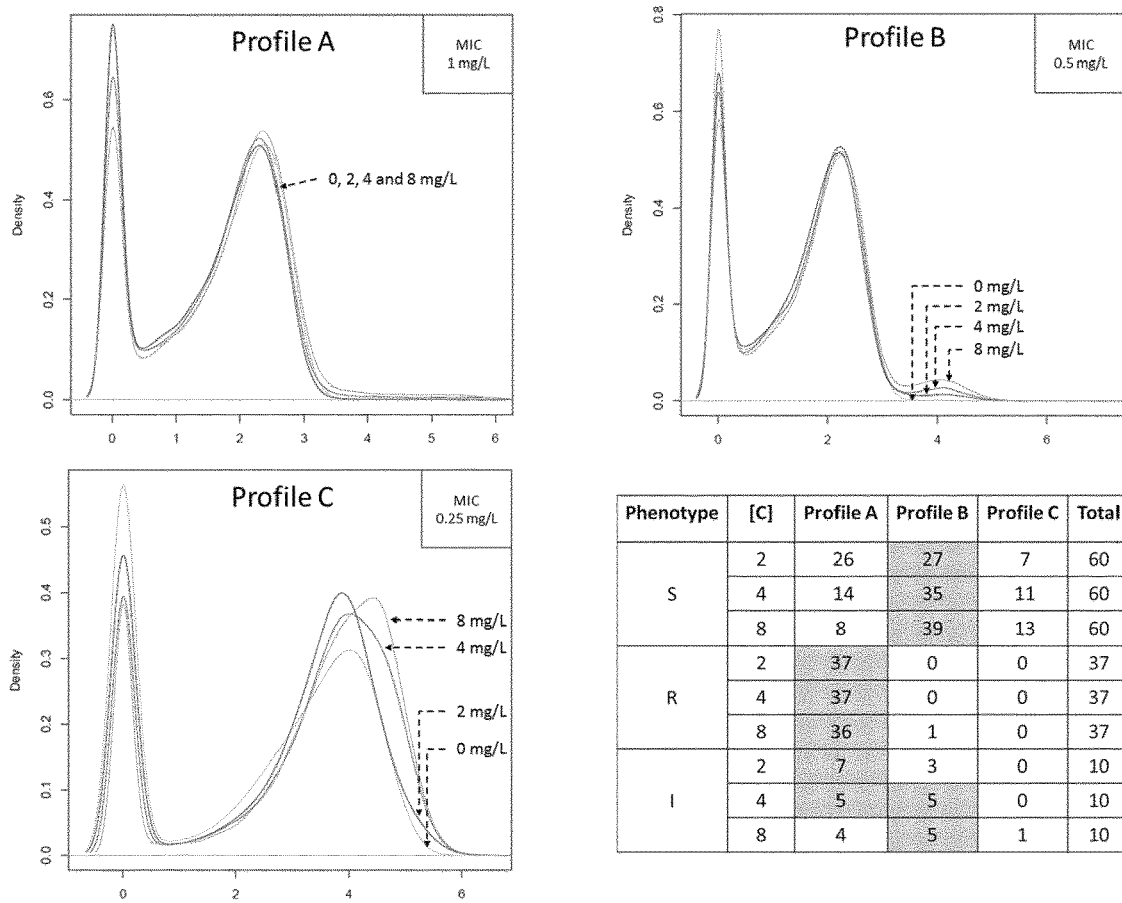
FIG. 7 is a schematic representation of fluorescence distribution profiles of Gentamicin-treated strains.

FCM fluorescence distribution obtained from Gentamicin-treated samples showed 3 main profiles when compared to untreated samples (FIG. 7: Spectra from 3 susceptible strains which are representative of the 3 main profiles A, B and C are shown. Within our panel of 107 strains, the number of strains exhibiting one of the three profiles are shown at each Gentamicin concentration investigated and for each phenotype (table). Cells filled in grey represent the highest number of strains exhibiting a specific profile for a given antibiotic concentration):
Profile A: no or slight shift of fluorescence distribution;
Profile B: heterogeneous distribution with one non fluorescent population and a small fluorescent population;

Profile C: Significant shift of the fluorescence distribution.

Within the panel of 107 strains, the distribution of profiles were approximately evaluated as follows (FIG. 7, table):

For the susceptible phenotype, equal number of strains exhibited either no shift (profile A) or heterogeneous fluorescence distributions (profile B) when treated with the lowest Gentamicin concentration (2 mg/L). When treated with 4 and 8 mg/L of Gentamicin, the majority of strains exhibited an heterogeneous fluorescence distribution (profile B);

Almost all (36 out of 37) resistant strains did not show any shift in fluorescence (profile A) at all concentrations tested;

For the intermediate phenotype, more strains showed no shift of fluorescence (profile A) when treated with the lowest concentration (2 mg/L). When treated with 4 and 8 mg/L of Gentamicin equal number of strains exhibited either no shift (profile A) or heterogeneous fluorescence distribution (profile B).

These observations suggest a predominance of heterogeneous fluorescence distributions for susceptible strains when treated with Gentamicin. The distribution profiles of resistant strains are highly consistent at all concentrations. Profile of intermediate strains are more variable depending on the concentrations used.

A.ii. Performance of Quantile-Based Vs. MFI-Based Prediction Models

As hypothesized above, the use of the MFI method might not be appropriate when heterogeneous fluorescence distributions are found. Relative to our observations within our panel of strains (FIG. 7), we have compared the performance of BPS prediction models that were built using feature vectors generated from quantile and MFI methods.

Following cross validation, our results show that the performance of prediction models are significantly higher for the quantile method when compared to MFI. All 4 prediction models generated with quantile-based feature vectors showed lower score values than the one built with MFI data (FIG. 8: The scores relative to the number of errors are shown for 4 prediction models generated with quantile feature vectors (q=0.75, q=0.9, q=0.95 q=0.99) and for 1 prediction model built with MFI feature vectors. For each histogram, the mean and the maximum score values are shown. The scales corresponding to the score values are shown on the left. The table at the bottom, shows the mean score values and the average number of prediction errors (mE, ME and VME). Total number of strains (Total), total number of susceptible strains (Total S) and total number of resistant strains (Total R) are also shown).

Figure 8:
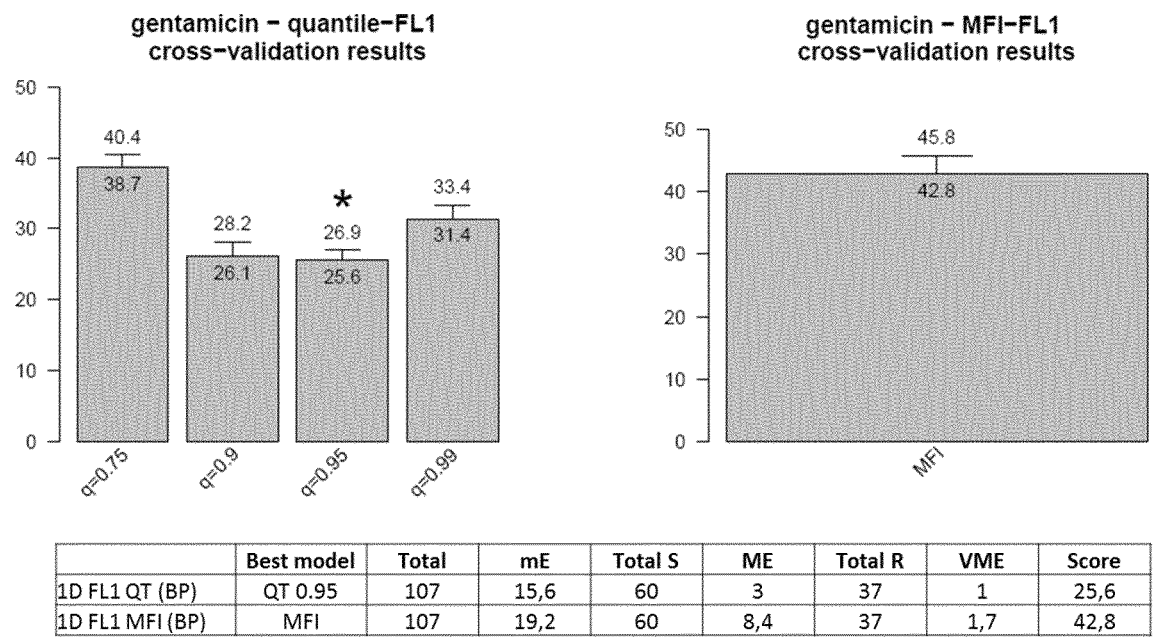
FIG. 8 is a schematic comparison of performance of 1D fluorescence prediction models (Quantile vs. MFI)

The performance of the best quantile-based model (q=0.95) was significantly better than the MFI-based model with a lower score and a higher percentage of category agreement with less of the 3 type of prediction errors (FIG. 8, table). The score values of the 4 prediction models built with quantile data, can also be represented as a parabolic-like curve that could be correlated with the small fluorescent population shown in FIG. 7 (profile B). This confirms the high potential of this small population in discriminating between phenotypes. Our results also suggest that a more in-depth investigation between q=0.9 and q=0.95 or between q=0.95 and q=0.99 could help to build a prediction model with better performance.

B. Experiment 2: In-Depth FCM Analysis and Selection of Prediction Models

B.i. Performance Evaluation of Discrimination Strategies

Figure 9:
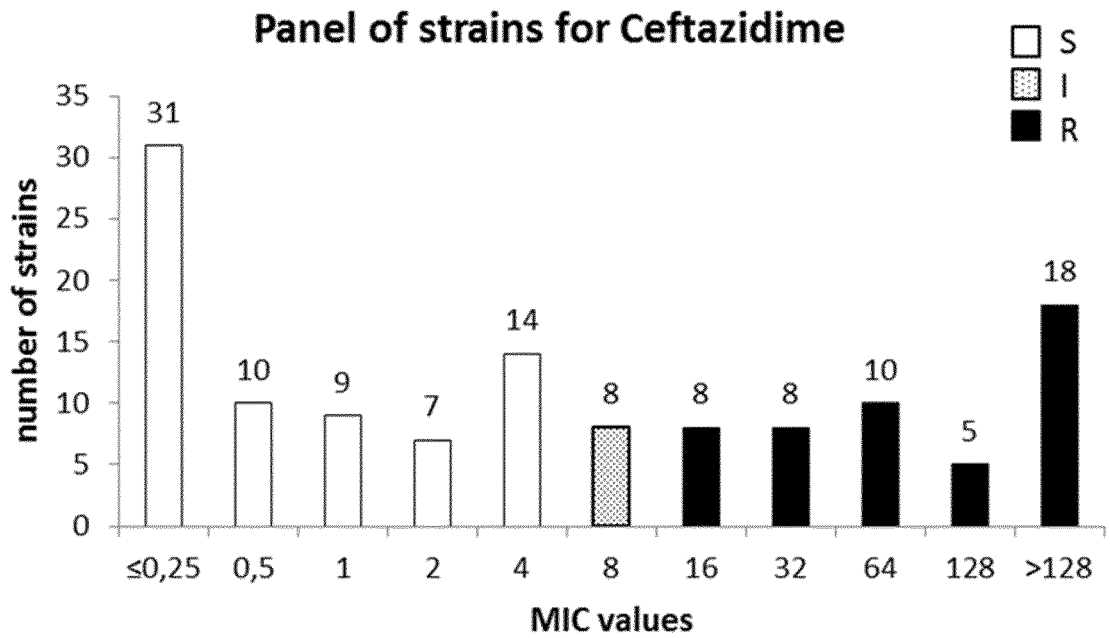
FIG. 9 is a schematic representation of the panel of strains according to their MICs for Ceftazidime.
Figures 10, 11:
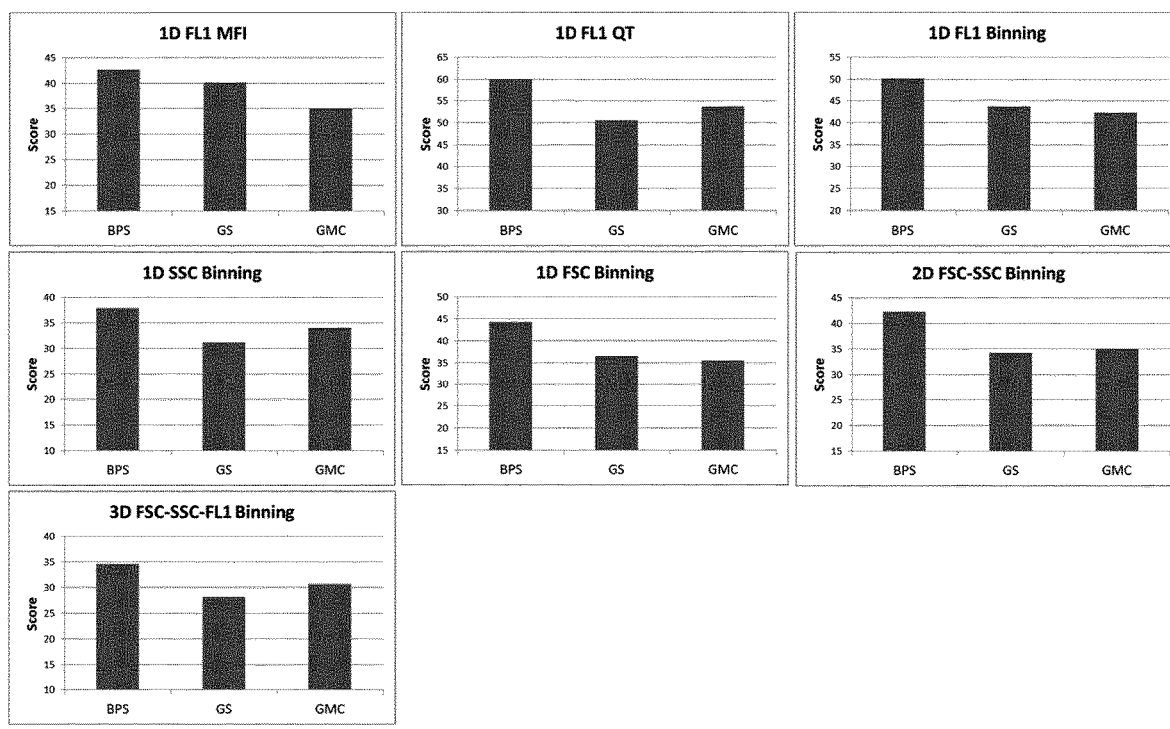
FIG. 10 is a table illustrating the number of predictions models generated.
FIG. 11 is a schematic comparison of discrimination strategies for Ceftazidime.

In this experiment, we have made an evaluation of wide range of prediction models for Ceftazidime:

128 Enterobacteriaceae strains (FIG. 9: Distribution of the panel of strains according to their MICs for Ceftazidime) were treated or not with four different concentrations of Ceftazidime (1, 2, 4 and 8 mg/L) using the FCM protocol described in FIG. 3;

FCM data were used to generate feature vectors as described above;

For each strategy (BPS, GS and GMS), 7 type of prediction models were built based on the feature vectors generated (FIG. 10: Number of predictions models generated. "FL1" means fluorescence);

The performance of all models were evaluated following cross validation as described above.

As shown in FIG. 10, 37 prediction models were generated for each discrimination strategy which makes a total number of 111 prediction models. The prediction model showing the lowest scores in each of the 7 type of prediction models was considered thereby leading to a condensed selection of 21 models. The GS and GMS strategies showed better discriminating performance (lower error scores) than the BPS strategy for all 7 type of prediction models generated (FIG. 11: Comparison of discrimination strategies for Ceftazidime. Each graph represents the lowest scores obtained for each of the 7 type of prediction models generated. The 3 strategies (BPS, GS and GMS) are compared.):

The GS strategy showed the lowest scores for 4 type of predictions models (1D FL1 QT, 1D SSC Binning, 2D FSC-SSC Binning and 3D FSC—SSC-FL1 Binning);

The GMS strategy showed the lowest scores for 3 type of predictions models (1D FL1 MFI, 1D FL1 Binning and 1D FCS Binning)

B.ii. Selection of the Best Prediction Model for Ceftazidime

The condensed selection of 21 prediction models were classified according to their error scores (FIG. 12: Classification of prediction models for Ceftazidime. BP=BPS. G=GS. GMC=GMS). According to our classification, the best prediction models for Ceftazidime is a 3D FSC—SSC-FL1 model built with the GS strategy. One observes the following:

It is interesting to note that the 1D SSC Binning (GS) prediction algorithm also showed relatively good performance (FIG. 12). This suggests that the FL1 and FSC parameters only slight contribute to the discrimination potential of the 3D model algorithm selected. Therefore, our analysis method and classification of prediction models might help to significantly simplify the FCM-AST protocol (no viability marker needed for the 1D SSC Binning (GS) model) as well as FCM acquisition parameters (only SSC). On the other hand, we can assume that the use of a different viability marker can significantly improve the discrimination potential of the 3D model for even better prediction performance;

The prediction models built on quantile data are the less performing ones. This suggests that the majority of strains treated with Ceftazidime exhibit homogeneous distributions of fluorescence.

C. Experiment 3: Selection of Relevant Antibiotic Concentrations

As shown in FIG. 12, the best prediction model for Ceftazidime is a 3D model that was built using the GS strategy. This model processes four concentrations of Ceftazidime (1, 2, 4 and 8 mg/L). In an effort to investigate the relevance of these concentrations in the discriminating potential of the 3D model, we have used the Lasso analytical tool to build a 3D model based on GS strategy as described above.

The 3D prediction model obtained using the Lasso tool showed relatively good performance with an error score slightly higher the score of the 3D model obtained with SVM analysis (FIG. 13: Performance comparison of 3D prediction models (GS) and VITEK 2. The confusion matrices show the correlation and discrepancies between the reference phenotype and the phenotypes predicted by the 3D models and VITEK® 2 from bioMérieux. The table at the bottom, shows the mean score values and the average number of prediction errors (mE, ME and VME). Total number of strains (Total), total number of susceptible strains (Total S) and total number of resistant strains (Total R) are also shown. Non-relevant concentrations of Ceftazidime in the Lasso analysis are indicated.).

Our panel of strains was also investigated using our commercial VITEK 2 system. For the sake of comparison, we have not used the VITEK® 2 Advanced Expert System that corrects potential prediction errors through a more global interpretation of results from other antibiotics. Instead, the predicted phenotypes shown for VITEK 2 were interpreted only from MIC values obtained for Ceftazidime. Overall, the performance of our 3D models were comparable to that of the VITEK® 2 system (FIG. 13). This confirms the high phenotype discrimination power of our prediction models.

One observes that:
  The 3D model built with Lasso only uses two concentrations (2 and 8 mg/L) which suggests that we could reduce the number of concentrations to be used for the development a FCM-AST application for Ceftazidime;
  In our BPS strategy, the concentrations used are 4 mg/L in the susceptible phenotype matrix and 8 mg/L in the resistance phenotype matrix. In our Lasso analysis the concentration of 4 mg/L is non-relevant and 2 mg/L is preferentially used. This confirms that the most discriminating concentrations in FCM investigations are not necessarily breakpoint concentrations. This might explain why the 3D model built using the BP strategy is the least performing of the 3D models (FIG. 13).

REFERENCES

1. Huang, T. H., et al., *Rapid cytometric antibiotic susceptibility testing utilizing adaptive multidimensional statistical metrics*. Anal Chem, 2015. 87(3): p. 1941-9.
2. Alvarez-Barrientos, A., et al., *Applications of flow cytometry to clinical microbiology*. Clin Microbiol Rev, 2000. 13(2): p. 167-95.
3. Aghayee, S., et al., *Combination of fluorescence microscopy and nanomotion detection to characterize bacteria*. J Mol Recognit, 2013. 26(11): p. 590-595.
4. Shapiro, H. M. and N. G. Perlmutter, *Killer applications: toward affordable rapid cell-based diagnostics for malaria and tuberculosis*. Cytometry B Clin Cytom, 2008. 74 Suppl 1: p. S152-64.
5. Joux, F. and P. Lebaron, *Use of fluorescent probes to assess physiological functions of bacteria at single-cell level*. Microbes Infect, 2000. 2(12): p. 1523-35.
6. Martinez, O. V., et al., *The effect of some beta-lactam antibiotics on Escherichia coli studied by flow cytometry*. Cytometry, 1982. 3(2): p. 129-33.
7. Pina-Vaz, C., S. Costa-de-Oliveira, and A. G. Rodrigues, *Safe susceptibility testing of Mycobacterium tuberculosis by flow cytometry with the fluorescent nucleic acid stain SYTO 16*. J Med Microbiol, 2005. 54(Pt 1): p. 77-81.
8. Cohen, C. Y. and E. Sahar, *Rapid flow cytometric bacterial detection and determination of susceptibility to amikacin in body fluids and exudates*. J Clin Microbiol, 1989. 27(6): p. 1250-6.
9. Kerstens, M., et al., *Quantification of Candida albicans by flow cytometry using TO-PRO((R))-3 iodide as a single-stain viability dye*. J Microbiol Methods, 2013. 92(2): p. 189-91.
10. Boi, P., et al., *Evaluation of Escherichia coli viability by flow cytometry: A method for determining bacterial responses to antibiotic exposure*. Cytometry B Clin Cytom, 2015. 88(3): p. 149-53.
11. Nuding, S. and L. Zabel, Detection, *Identification, and Susceptibility Testing of Bacteria by Flow Cytometry*. J Bacteriol Parasitol 2013. S5-005.
12. Gauthier, C., Y. St-Pierre, and R. Villemur, *Rapid antimicrobial susceptibility testing of urinary tract isolates and samples by flow cytometry*. J Med Microbiol, 2002. 51(3): p. 192-200.
13. Gant, V. A., et al., *The application of flow cytometry to the study of bacterial responses to antibiotics*. J Med Microbiol, 1993. 39(2): p. 147-54.
14. Wickens, H. J., et al., *Flow cytometric investigation of filamentation, membrane patency, and membrane potential in Escherichia coli following ciprofloxacin exposure*. Antimicrob Agents Chemother, 2000. 44(3): p. 682-7.
15. Renggli, S., et al., *The role of auto-fluorescence in flow-cytometric analysis of Escherichia coli treated with bactericidal antibiotics*. J Bacteriol, 2013.
16. J. L., F. G., Method for the rapid determination of susceptibility or resistance of bacteria to antibiotics EP 2821499 A1 2015.
17. Pina-Vaz, C., et al., Kit and method of detecting the resistant microorganisms to a therapeutic agent. WO 2012/164547 A1, 2012.
18. Suller, M. T., J. M. Stark, and D. Lloyd, *A flow cytometric study of antibiotic-induced damage and evaluation as a rapid antibiotic susceptibility test for methicillin-resistant Staphylococcus aureus*. J Antimicrob Chemother, 1997. 40(1): p. 77-83.
19. Jepras, R. I., et al., *Rapid assessment of antibiotic effects on Escherichia coli by bis-(1,3-dibutylbarbituric acid) trimethine oxonol and flow cytometry*. Antimicrob Agents Chemother, 1997. 41(9): p. 2001-5.
20. Shrestha, N. K., et al., *Rapid differentiation of methicillin-resistant and methicillin-susceptible Staphylococcus aureus by flow cytometry after brief antibiotic exposure*. J Clin Microbiol, 2011. 49(6): p. 2116-20.
21. Shrestha, N. K., et al., *Immuno-flow cytometry for the rapid identification of Staphylococcus aureus and the detection of methicillin resistance*. Eur J Clin Microbiol Infect Dis, 2012. 31(8): p. 1879-82.
22. M. Yuan and Y. Lin, *Model selection and estimation in regression with grouped variables*. Journal of The Royal Statistical Society Series B, 68(1):49-67, 2006.
23. F. Bach et al., *Structured sparsity through convex optimization*. Statistical Science, 27(4):450-468, 2012.

The invention claimed is:
1. A method for quantifying sensibility of a test microorganism to a concentration of an antimicrobial agent, comprising:
  preparing at least two liquid samples comprising a population of the test microorganism and a viability fluo- rescence marker targeting the test microorganism in which at least one of the liquid samples comprises the antimicrobial agent at the concentration and another of the liquid samples does not comprise the antimicrobial agent;

performing flow cytometry on the liquid samples with a flow cytometer so as to acquire a digital set of values comprising a fluorescence distribution and/or a forward scatter distribution and/or a side scatter distribution of the population of test microorganism in each of the liquid samples, wherein:

the flow cytometer comprises a fluidic system, at least one light source, an optical system comprising excitation optics and collection optics, and an electronic system; and an acquired distribution of each sample is subject to computation to calculate:

a first coordinate value corresponding to the main mode of the acquired distribution;

a first area of the acquired distribution for values greater than the first coordinate value;

a second coordinate value that is greater than the first coordinate value;

a second area of the acquired distribution between the first and second coordinate values that equals a predefined percentage of the first area over 50%; and a ratio according to the relation:

$$Q = \frac{QT(ATB) - \text{Mode}(ATB)}{QT(\text{no } ATB) - \text{Mode}(\text{no } ATB)}$$

where QT is a notation for quantile and ATB is a notation for the antimicrobial agent, Mode (ATB) and QT(ATB) are respectively the first and second coordinate values with the concentration of the antimicrobial agent, and Mode(no ATB) and QT(no ATB) are respectively the first and second coordinate values without any concentration of the antimicrobial agent.

2. The method according to claim 1, wherein the acquired distribution comprises the fluorescence distribution and the coordinate values are fluorescence values.

3. The method according to claim 2, wherein:
a system comprises the flow cytometer and a computer unit connected to the flow cytometer; and
the system is installed in a clinical laboratory so that the method is performed in the clinical laboratory.

4. The method according to claim 2, wherein the predefined percentage of the first area is over 70%.

5. The method according to claim 2, wherein the antimicrobial agent is an antibiotic and the population of test microorganism are bacteria.

6. A method for providing a prediction model of sensibility phenotype to an antimicrobial agent amongst susceptible, intermediate, and resistant phenotypes, comprising a learning stage that comprises:

choosing a set of microorganisms comprising susceptible, intermediate, and resistant phenotype microorganisms in which the phenotypes are determined based on susceptible and resistant breakpoint concentrations of the antimicrobial agent so as to generate a digital set of sensibility phenotypes of the set of microorganisms;

preparing liquid samples for each microorganism of the set of microorganisms comprising a population of the microorganism, a viability fluorescence marker targeting the microorganism, and the antimicrobial agent in which the liquid samples comprises at least two different concentrations of the antimicrobial agent;

performing flow cytometry on the liquid samples with a flow cytometer so as to acquire a digital set of values comprising a fluorescence distribution and/or a forward scatter distribution and/or a side scatter distribution of the population of microorganism in each of the liquid samples; and generating a feature vector based on the sets of values acquired for each microorganism of the set of microorganisms via a computer unit, wherein:

the flow cytometer comprises a fluidic system, at least one light source, an optical system comprising excitation optics and collection optics, and an electronic system; and generation of the feature vector for each of the different concentrations of the antimicrobial agent comprises computing:

a first coordinate value corresponding to the main mode of an acquired distribution;

a first area of the acquired distribution for values greater than the first coordinate value;

a second coordinate value that is greater than the first coordinate value;

a second area of the acquired distribution between the first and second coordinate values that equals a predefined percentage of the first area over 50%; and a ratio according to the relation:

$$Q = \frac{QT(ATB) - \text{Mode}(ATB)}{QT(\text{no } ATB) - \text{Mode}(\text{no } ATB)}$$

where QT is a notation for quantile and ATB is a notation for the antimicrobial agent, Mode(ATB) and QT(ATB) are respectively the first and second coordinate values with the concentration of the antimicrobial agent, and Mode(no ATB) and QT(no ATB) are respectively the first and second coordinate values without any concentration of the antimicrobial agent; and learning via the computer unit so as to provide a prediction model of the sensibility phenotype to the antimicrobial agent based on the generated feature vectors and the digital set of sensibility phenotypes.

7. The method according to claim 6, further comprising a prediction stage that comprises:

preparing liquid samples comprising a population of a test microorganism, the viability fluorescence marker, and the antimicrobial agent at different concentrations;

performing flow cytometry on the liquid samples to acquire a digital set of values corresponding to the set of values acquired in the learning stage for each sample of the test microorganism;

generating a feature vector based on the sets of values acquired for the test microorganism via the computer unit corresponding to the feature vectors generated in the learning stage; and predicting the sensibility phenotype of the test microorganism with the prediction model by applying the prediction model to the feature vector of the test microorganism.

8. The method according to claim 6, wherein:
the prediction model comprises a first prediction model of the susceptible phenotype versus the resistant and intermediate phenotypes and a second prediction model of the resistant phenotype versus the susceptible and intermediate phenotypes in which the first and second prediction models are learned independently; and the intermediate phenotype is predicted when the first prediction model does not predict the susceptible phenotype and when the second prediction model does not predict the resistant phenotype.

9. The method according to claim 6, wherein the prediction model comprises a first prediction model of the susceptible phenotype versus the resistant and intermediate phenotypes, a second prediction model of the resistant phenotype versus the susceptible and intermediate phenotypes, and a third prediction model of the intermediate phenotype versus the susceptible and resistant phenotypes in which the first, second, and third prediction models are learned independently.

10. The method according to claim 6, wherein the different concentrations of the antimicrobial agent define a range comprising the susceptible and resistant breakpoint concentrations.

11. The method according to claim 6, wherein the different concentrations of the antimicrobial agent are the susceptible and resistant breakpoint concentrations.

12. The method according to claim 6, wherein the different concentrations of the antimicrobial agent comprise at least three concentrations.

13. The method according to claim 6, wherein at least one of the different concentrations of the antimicrobial agent is less than the susceptible breakpoint concentration.

14. The method according to claim 6, comprising, at the learning stage, selection of the different concentrations of the antimicrobial agent by:
    selecting a first set of different concentrations comprising the different concentrations of the antimicrobial agent; and
    learning a prediction model of the sensibility phenotype to the antimicrobial agent based on the generated feature vectors and the digital set of sensibility phenotypes, wherein:
    the learning the prediction model is performed using a L1-regularised optimization problem trading off precision of the prediction model and complexity of the prediction model; and
    the different concentrations of the antimicrobial agent are the concentrations of the first set of concentrations that are not discarded by the L1-regularised optimization problem.

15. The method according to claim 14, wherein the L1-regularised optimization problem is a L1-regularized logistic regression.

16. The method according to claim 6, wherein the microorganisms of the set of microorganisms belong to different species and/or genera.

17. The method according to claim 6, wherein the predefined percentage of the first area is over 70%.

18. A method for predicting sensibility phenotype of a test microorganism to an antimicrobial agent amongst susceptible, intermediate and resistant phenotypes, comprising:
    preparing liquid samples comprising a population of the test microorganism, a viability fluorescence marker targeting the test microorganism, and the antimicrobial agent at different concentrations;
    performing flow cytometry on the liquid samples with a flow cytometer to acquire a digital set of values comprising a fluorescence distribution and/or a forward scatter distribution and/or a side scatter distribution of the population of the test microorganism for each sample of the test microorganism;
    generating a feature vector based on the sets of values acquired for the test microorganism via a computer unit; and
    predicting the sensibility phenotype of the test microorganism via the computer unit storing a prediction model by applying the prediction model to the feature vector of the test microorganism, wherein:
    the flow cytometer comprises a fluidic system, at least one light source, an optical system comprising excitation optics and collection optics, and an electronic system; and
    the prediction model is learned by the method according to claim 6.

19. The method according to claim 18, wherein the set of values comprises the fluorescence distribution.

20. The method according to claim 19, wherein:
    a system comprises the flow cytometer and a computer unit connected to the flow cytometer; and
    the system is installed in a clinical laboratory so that the method is performed in the clinical laboratory.

21. The method according to claim 19, wherein the antimicrobial agent is an antibiotic and the population of test microorganism are bacteria.

22. A system for predicting sensibility phenotype of a test microorganism to an antimicrobial agent amongst susceptible, intermediate and resistant phenotypes, comprising:
    a flow cytometer comprising a fluidic system, at least one light source, an optical system comprising excitation optics and collection optics, and an electronic system in which the flow cytometer is configured to acquire a digital set of values comprising a fluorescence distribution and/or a forward scatter distribution and/or a side scatter distribution of a population of the test microorganism in liquid samples wherein the liquid samples comprise a viability fluorescence marker targeting the test microorganism and different concentrations of the antimicrobial agent; and
    a computer unit configured for:
    storing the prediction model learned by the method according to claim 6;
    generating a feature vector based on the sets of values acquired for the test microorganism; and
    predicting the sensibility phenotype of the test microorganism by applying the prediction model to the feature vector of the test microorganism.

23. A computer readable medium storing instruction for executing a method with a computer to predict sensibility phenotype of a test microorganism to an antimicrobial agent amongst susceptible, intermediate and resistant phenotypes, the method comprising:
    generating a feature vector based on sets of values acquired for a test microorganism in which the sets of values comprise a fluorescence distribution and/or a forward scatter distribution and/or a side scatter distribution of a population of the test microorganism in liquid samples acquired by a flow cytometer; and
    predicting the sensibility phenotype of the test microorganism by applying a prediction model to the feature vector of the test microorganism,
    wherein the prediction model is learned by the method according to claim 6.

* * * * *